US007378445B2

(12) United States Patent
Aylward et al.

(10) Patent No.: US 7,378,445 B2
(45) Date of Patent: May 27, 2008

(54) TREATMENT OF PROSTATE CANCER

(75) Inventors: James Harrison Aylward, Indooroopilly (AU); Peter Gordon Parsons, St. Lucia (AU)

(73) Assignee: Peplin Research Pty. Ltd., Queensland (AU)

( * ) Notice: Subject to any disclaimer, the term of this patent is extended or adjusted under 35 U.S.C. 154(b) by 0 days.

(21) Appl. No.: 11/324,587

(22) Filed: Jan. 3, 2006

(65) Prior Publication Data

US 2006/0105994 A1   May 18, 2006

Related U.S. Application Data

(63) Continuation of application No. 10/149,301, filed as application No. PCT/AU01/00966 on Aug. 7, 2001, now abandoned.

(30) Foreign Application Priority Data

Aug. 7, 2000   (AU) .................................. PQ 9231

(51) Int. Cl.
 *A61K 31/22* (2006.01)
 *C07C 69/52* (2006.01)
(52) U.S. Cl. ...................... 514/549; 560/205
(58) Field of Classification Search ............ 514/549, 514/546; 560/205
 See application file for complete search history.

(56) References Cited

U.S. PATENT DOCUMENTS

| 4,418,064 | A | 11/1983 | Powell et al. |
| 4,560,774 | A | 12/1985 | Pettit et al. |
| 4,716,179 | A | 12/1987 | Hecker et al. |
| 5,145,842 | A | 9/1992 | Driedger et al. |
| 5,643,948 | A | 7/1997 | Driedger et al. |
| 5,716,968 | A | 2/1998 | Driedger et al. |
| 5,750,568 | A | 5/1998 | Driedger et al. |
| 5,886,017 | A | 3/1999 | Driedger et al. |
| 5,886,019 | A | 3/1999 | Driedger et al. |
| 5,891,870 | A | 4/1999 | Driedger et al. |
| 5,891,906 | A | 4/1999 | Driedger et al. |
| 5,932,613 | A | 8/1999 | Jiang et al. |
| 5,962,498 | A | 10/1999 | Driedger et al. |
| 6,268,395 | B1 | 7/2001 | Hattori |
| 6,432,452 | B1 | 8/2002 | Aylward et al. |
| 6,593,371 | B1 | 7/2003 | Staggs |
| 6,787,161 | B2 | 9/2004 | Aylward et al. |
| 6,844,013 | B2 | 1/2005 | Aylward et al. |
| 2003/0166613 | A1 | 9/2003 | Aylward et al. |
| 2003/0171334 | A1 | 9/2003 | Aylward et al. |
| 2003/0171337 | A1 | 9/2003 | Aylward et al. |
| 2003/0195168 | A1 | 10/2003 | Aylward et al. |
| 2005/0003031 | A1 | 1/2005 | Aylward et al. |
| 2005/0209192 | A1 | 9/2005 | Aylward et al. |

FOREIGN PATENT DOCUMENTS

| CN | 1077129 | 10/1993 |
| CN | 1105246 | 7/1995 |
| CN | 1112011 | 11/1995 |
| CN | 1131037 | 9/1996 |
| DE | 29 02 506 | 1/1979 |
| EP | 0 330 094 | 8/1989 |
| EP | 0 455 271 | 11/1991 |
| EP | 0 310 622 | 4/1992 |
| JP | 8-13571 | 1/1996 |
| JP | 8-176002 | 7/1996 |
| JP | 8-245505 | 9/1996 |
| WO | WO 87/07599 | 12/1987 |
| WO | WO 97/15575 | 5/1997 |
| WO | 99/08994 | 2/1999 |

OTHER PUBLICATIONS

M. Belkin et al., "Tumor-Damaging Capacity of Plant Materials". I. Plants Used as Cathartics, *National. Cancer Institute.*, 13: 139-149 (1952).
D. Weedon et al., "Home Treatment of Basal Cell Carcinoma", *Med. J. Aust.*, 1:928 (1976).
Uemura, D.. et al., "New Diterpene, 13-Oxyingenol, Derivative Isolated from Euphorbia Kansui Liou", *Tetrahedron Letters* 29: 2529-2532 (1974).
Kupchan S.M. et al., "Antileukemic Principles Isolated From Euphorbiaceae Plants" *Science*, 191: 571-572 (1975).
Kupchan S.M. et al., "Gnidimacrin and Gnidimacrin 20-Palmitate, Novel Macrocyclic Antileukemic Diterpenoid Esters From *Gnidia Subcordata*", *Communications to the Editor*: 5719-5720 (1976).
Evans, F.J. et al., "The Tigliance, Daphane and Ingenane Diterpenes, Their Chemistry, Distribution and Biological Activities, A Review," *Lloydia* 41(3): 193-233 (1978).
Hecker E., "Structure-Activity Relationships in Diterpene Esters Irritant and Cocarcinogenic to Mouse Skin", *Carcinogenesis* 2: 11-48 (1978).
Seip E.H. et al., "Skin Irritant Ingenol Esters from *Euphorbia Esula*", *Planta Medica* 46: 215-218 (1982).
Nishizuka Y., "The Role of Protein Kinase C in Cell Surface Signal Tranduction and Tumour Promotion", *Nature* 308: 693-698 (1984).
Schmidt R.J., "The Ingenane Polyol Esters", *Naturally Occurring Phorbol Esters*, Boca Raton: CRC Press: 245-269 (1986).
Inoue S. et al., "Ingenane Synthetic Studies. Sterocontrolled Introduction Of All Oxygenated And Unsaturated Centers In An Ingenol Prototype", *J. Org. Chem.* 52: 5497-5498 (1987).
Hamamoto Y. et al., "Comparison of Effects of Protein Kinase C Inhibitors on Phorbol Ester-Induced CD4 Down-Regulation and Augmentation of Human Immunodeficiency Virus Replication In Human Cell Lines", *Biochemical and Biophysical Research Communications* 164(1): 339-344 (1989).

(Continued)

*Primary Examiner*—Charanjit S. Aulakh
(74) *Attorney, Agent, or Firm*—Scully, Scott, Murphy & Presser, P.C.

(57) ABSTRACT

A chemical agent of the diterpene family obtained from a member of the Euphorbiaceae family of plants for use in the treatment of prophylaxis of prostate cancer or a related cancer or condition.

24 Claims, 8 Drawing Sheets

OTHER PUBLICATIONS

Chowdhury I.H. et al., The Phorbol Ester TPA Strongly Inhibits HIV-1-Induced Syncytia Formation but enhances Virus Production: Possible Involvement of Protein Kinase C Pathway, *Virology* 176: 126-132 (1990).

Laurence J. et al., "Phorbol Ester-Mediated Induction of HIV-1 from A Chronically Infected Promonocyte Clone: Blockade by Protein Kinase Inhibotors and Relationships to Tat-Directed Trans-Activation", *Biochemical and Biophysical Research Communications* 166(1): 349-357 (1990).

Krauter, et al., "Structure/activity relationships of polyfunctional diterpenes of tigliane type" *Eur. J. Biochem*, 242: 417-427 (1996).

El-Merzabani, et al., "Screening System for Egyptian Plants with Potential Anti-tumour Activity", *Planta Medica*.36: 150-155 (1979).

Benjamini, El et al. "Immunology"—*A Short Course*: 15-18 (1988).

Abo, K.A. "Fitoterpia", LIX(3): 244-246 (1988).

Alastair Aitken et al., "The Activation of Protein Kinase C by Daphnane, Ingenane and Tigliane Diterpenoid Esters", *Botanical Journal of the Linnean Society*, 94: 247-263 (1987).

Sahar El-Mekkaway et al., "Anti-HIV-1 Phorbol Esters from the Seed of *Croton Tiglium*", *Phytochemistry*, 53: 457-464 (2000).

U.S. Appl. No. 11/324,587, Aylward et al.

Evans, F.J. et al, "Pro-Inflammatory, Tumor-Promoting and Anti-Tumor Diterpenes of the Plant Families *Euphoribiaceae* and *Thymelaeaceae*" *Department of Pharmacognosy, The School of Pharmacy, University of London*, 44: 90-99.

Tian-Shung Wu et al., "Antitumor Agents, 119[1] Kansuiphorins A and B, Two Novel Antileukemic Diterpene Esters From *Euphorbia Kansui*", *Journal of Natural Products*, 54(3): 823-829 (1991).

Salah M.A.D. Zayed et al., "Dietary cancer risk from conditional cancerogens in produce of livestock fed on species of spruge (*Euphorbiaceae*) 1. Skin irritant and tumor promoters of the ingenane diterpene ester type", *Cancer Res. Clin. Oncol*, 124: 131-140 (1998).

B D Curti "Physical Barriers to Drug Delivery in Tumors", Critical Reviews in Onocology/Hematology, 14 : 29-39 (1992).

G. B. Dermer, "Another Anniversary for the War on Cancer" *Bio/Technology*, 12: 320 (1994).

T. Gura, "Systems for Identifying New Drugs are Often Faulty", *Science*, 278: 1041-1042 (1997).

R.I. Freshney, "Culture of Animal Cells, A Manual of Basic Technique", *Department of Clinical Oncology, Cancer Research Campaign Laboratories, University Glasgow*.

L H Hartwell, et al. "Integrating Genetic Approaches in the Discovery of Anticancer Drugs," *Science*, 278: 1064-1068 (1997).

R K Jain, "Barriers to Drug Delivery in Solid Tumors", *Scientific American*: 58-65 (1994).

"Extract from Endocrinology, Proceedings of the American Association for Cancer Research", 36: 256 (1995).

Hohmann, et al. "Jatrophane Diterpenoids from *Euphorbia peplus*", *Phytochemicstry*, 51: 673-677 (1999).

Hohmann, et al. "Diterpenoids from *Euphorbia peplus*", Plant Med. 66: 291-294 (2000).

Zayed, et al., Dietry risk from conditional cancerogens in produce of livestock fed on species of spurge (*Euphorbiaceae*) III. Milk of lactating goats fed on the skin irritant herb Eupho, *J. Cancer Research & Clinical Oncology*, 124(6): 301-306 (1998).

Zayed, et al., Dietry cancer risk conditional cancerogens in produce of livestock fed on species of spurge (*Euphorbiaceae*) III. Skin irritant and tumor-promoting ingenane-type diterpene este, *J. Cancer Research & Clinical Oncolgy*, 124: 131-140 (1998).

Wu et al., Kansuiphorins A and B, two novel antileukemic diterpene esters from *Euphorbia Kansui*, Antitumour Agents, *J. of Natural Products* 54(3): 823-829 (1991).

Mandell, Douglas and Bennett's Principles and Practice of Infectious Diseases. 4th Edition (1995): 1314-1323; 1330-1335 and 1590-1603.

TREATMENT OF PROSTATE CANCER

RELATED APPLICATION

This application is a continuation of Application U.S. Ser. No. 10/149,301, filed in the United States Patent and Trademark Office on Feb. 24, 2003 now abandoned, which is a '371 of PCT/AU01/00966, filed on Aug. 7, 2001.

FIELD OF THE INVENTION

The present invention relates generally to chemical agents useful in treatment and prophylaxis of prostate cancer or a related cancer or condition or in the amelioration of symptoms resulting from or facilitated by prostate cancer or a related cancer or condition in a mammalian animal including human or primate. More particularly, the present invention provides a chemical agent of the diterpene family obtained from a member of the Euphorbiaceae family of plants or botanical or horticultural relatives thereof or derivatives or chemical analogs or chemically synthetic forms of the agents for use in the treatment or prophylaxis of prostate cancer or a related cancer or condition or in the amelioration of symptoms resulting from or facilitated by prostate cancer or a related cancer or condition in a mammal and in particular a human. The present invention further contemplates a method for the prophylaxis or treatment of a mammalian subject presenting with prostate cancer or a related cancer or condition or with symptoms of prostate cancer or a related cancer or condition by topical or systemic administration of a diterpene obtainable from a member of the Euphorbiaceae family or botanical or horticultural relatives thereof or a derivative, chemical analog or chemically synthetic form of the agent. The chemical agent of the present invention may be in the form of a purified compound, mixture of compounds, a precursor form of one or more of the compounds capable of chemical transformation into a therapeutically active agent or be in the form of a chemical fraction, sub-fraction or preparation or extract of the plant. The present invention particularly relates to the treatment of either hormone-resistant or hormone-sensitive prostate cancer or metastatic prostate cancer using a chemical agent or fraction from the sap of *Euphorbia pephli*. The chemical agents or chemical fractions of the present invention may be given alone or in combination with other cancer symptom-ameliorating chemical or physical agents and/or other therapeutic interventions including interventionist procedures.

BACKGROUND OF THE INVENTION

Bibliographic details of the publications referred to by author in this specification are collected at the end of the description.

Reference to any prior art in this specification is not, and should not be taken as, an acknowledgment or any form of suggestion that this prior art forms part of the common general knowledge in Australia or any other country.

As the most common internal cancer in older men and the seventh most common cause of death in men of all ages in developed countries, cancer of the prostate is a serious health problem in terms of drawn-out personal suffering and premature death not to mention the cost to the health care system. The incidence of prostate cancer appears to be increasing, over and above improved detection rates in recent years (Post et al., 1999). Although many men with cancer of the prostate die from other causes, the high incidence results in significant morbidity and death directly from the prostatic tumor. Currently-available therapy carries a significant risk of major side effects, including incontinence and impotence, and consequently many men are reluctant to accept treatment at an early stage of the disease. The need to improve the treatment of prostate cancer is underlined by the existence of over 150 clinical trials world wide (Future Oncology, vol. 4, number 3, 1998), including 34 new or modified products (http://www.phrma.org/idf/charts/cancer99.pdf).

Hormone-resistant bony secondaries (hrbs) are universally found in the natural history of advanced prostate cancer and are resistant to all current chemotherapy. They cause severe pain, prolonged hospitalization, pathological fractures, spinal-cord compression and paraplegia, and may be fatal. External beam radiotherapy is the mainstay of palliative treatment. However, it can only be used once for a given bony secondary. A range of bone-seeking compounds can image prostate cancer metastases (Bushnell et. al., 1999; Norris et al., 1999). Parenteral strontium isotopes have had limited success for treatment but their use is limited by their toxicity to the bone narrow, especially platelets. Bisphosphonates (osteoclast inhibitors) may decrease the bone pain in a few cases, but again are generally disappointing and do not increase life expectancy.

There is a need, therefore, to develop more effective therapeutic protocols and more efficacious therapeutic agents to assist in the treatment of this disease.

Natural product screening is a term applied to the screening of natural environments for bioactive molecules. Particularly sought after bioactive molecules are those having potential as useful therapeutic agents. Natural environments include plants, microorganisms, coral and marine animals. The search for potential therapeutic agents for the treatment of cancer and infection by pathogenic organisms remains an important focus.

The Euphorbiaceae family of plants covers a wide variety of plants including weeds and other types of plants of *Euphorbia* species. There has been a variety of inconclusive reports on the potential effects of the sap of these plants on a range of conditions as well as promoting tumorigenesis and causing skin and ocular irritation.

The most intensively studied species of this group is *Euphorbia pilulifera* L (synonyms *E. hirta* L., *E. capitata* Lam.), whose common names include pill-bearing spurge, snakeweed, cat's hair, Queensland asthma weed and flowery-headed spurge. The plant is widely distributed in tropical countries, including India, and in Northern Australia, including Queensland.

A recent report describes selective cytotoxicity of a number of tigliane diterpene esters from the latex of *Euphorbia poisonii*, a highly toxic plant found in Northern Nigeria, which is used as a garden pesticide. One of these compounds has a selective cytotoxicity for the human kidney carcinoma cell line A-498 more than 10,000 times greater than that of adriamycin (Fatope et al., 1996).

*Euphorbia hirta* plants and extracts thereof have been considered for a variety of purposes, including tumor therapy (European Patent Application No. 0 330 094), AIDS-related complex and AIDS (Hungarian Patent Application No. 208790) and increasing immunity and as an anti-fungoid agent for treatment of open wounds (German Patent Application No. 4102054).

Thus, while there are isolated reports of anti-cancer activity of various *Euphorbia* preparations (see Fatope et al., 1996; Oksuz et al., 1996), not only are the compounds present in at least one *Euphorbia* species reported to be carcinogenic (Evans and Osman, 1974; Stavric and Stolz, 1976; Hecker, 1970), but at least one species has a skin-irritant and tumor-promoting effect (Gundidza and Kufa, 1993) and another species reduces EBV-specific cellular immunity in Burkitt's lymphoma (Imai, 1994).

In accordance with the present invention, the inventors have identified chemical agents and fractions comprising these agents from a plant of the Euphorbiaceae family which are useful in the treatment and prophylaxis of prostate cancer in mammalian and in particular human subjects.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The present invention is predicated in part on the identification of chemical agents and fractions comprising same from plants of the Euphorbiaceae family and in particular *Euphorbia peplus* which are useful in the treatment and prophylaxis of prostate cancer or a related cancer or condition. The chemical agents or fractions comprising same are particularly useful for the treatment or prophylaxis of, or in the amelioration of symptoms associated with, prostate cancer including metastatic prostate cancer.

Accordingly, one aspect of the present invention contemplates a method for the treatment or prophylaxis of prostate cancer or a related cancer or condition in a subject, said method comprising the administration to said subject of a symptom-ameliorating effective amount of a chemical agent obtainable from a plant of the Euphorbiaceae family or a derivative or chemical analog thereof which chemical agent is a diterpene selected from compounds of the ingenane, pepluane and jatrophane families and which chemical agent or derivative or chemical analog is represented by any one of the general formulae (I)-(V) as defined herein and wherein said chemical agent or its derivatives or chemical analogs is administered for a time and under conditions sufficient to ameliorate one or more symptoms associated with said prostate cancer.

More particularly, the present invention is directed to a method for the treatment or prophylaxis of prostate cancer or a related cancer or condition in an subject, said method comprising the administration to said subject of a symptom-ameliorating effective amount of a chemical agent obtainable from *E. peplus* or a derivative or chemical analog thereof which chemical agent is a diterpene selected from compounds of the ingenane, pepluane and jatrophane families and which chemical agent or derivative or chemical analog is represented by any one of the general formulae (I)-(V) as defined herein and wherein said chemical agent or its derivatives or chemical analogs is administered for a time and under conditions sufficient to ameliorate one or more symptoms associated with said prostate cancer.

Another aspect of the present invention contemplates a method for the immunopotentiation of a subject in the treatment and prophylaxis of said subject for prostate cancer or a related cancer or condition, said method comprising the administration to said subject of a symptom-ameliorating effective amount of a diterpene, or a chemical fraction comprising same from a plant of the family Euphorbiaceae or a derivative or chemical analog of said diterpene having the structures as defined herein against prostate cancer cells.

Yet another aspect of the present invention contemplates a method for the treatment or prophylaxis of a subject with prostate cancer or a related cancer or condition or with the symptoms of prostate cancer, said method comprising the administration to said subject of a symptom-ameliorating effective amount of an angeloyl-substituted ingenane or a chemical fraction or plant extract comprising same.

Still another aspect of the present invention provides a method for the treatment or prophylaxis of a subject with prostate cancer or a related cancer or condition or with the symptoms of prostate cancer, said method comprising the administration to said subject of a symptom-ameliorating effective amount of one or more of ingenol-3-angelate, 20-deoxy-ingenol-3-angelate and/or 20-O-acetyl-ingenol-3-angelate or a derivative thereof or a pharmaceutically acceptable salt of these or a chemical fraction or plant extract comprising same.

Even yet another aspect of the present invention contemplates a method for the treatment or prophylaxis of prostate cancer or a related cancer or condition in a subject, said method comprising the simultaneous or sequential administration to said subject of a symptom-ameliorating effective amount of a chemical agent derived from a plant of the Euphorbiaceae family as hereinbefore described together with a therapeutic protocol or a symptom-ameliorating effective amount of another chemical agent or a physical agent.

A further aspect of the present invention also provides a composition for treatment and/or prophylaxis of prostate cancer or a related cancer or condition in a subject, comprising one or more chemical agents of the present invention, together with a pharmaceutically acceptable carrier and/or diluent, and optionally one or more other active compounds.

Yet another aspect of the present invention encompasses the use of one or more chemical agents of the present invention and optionally one or more other active compounds in the preparation of a medicament for the treatment and/or prophylaxis of prostate cancer or a related cancer or condition.

Figure 1:
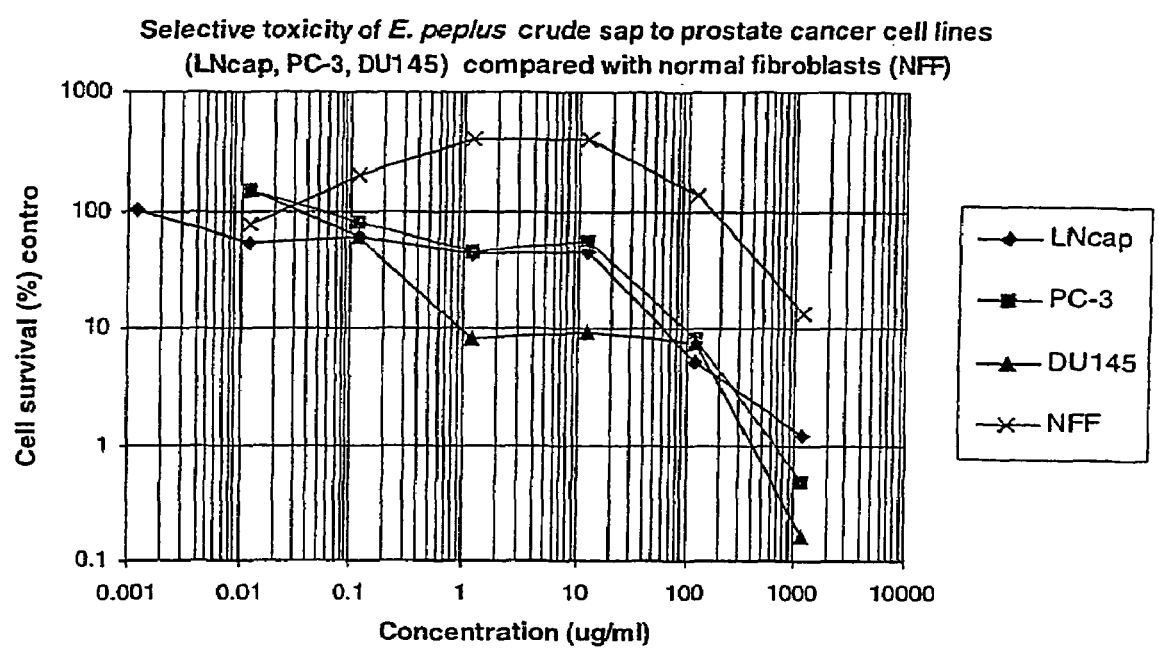
FIG. 1 is a diagrammatic representation illustrating the selective toxicity of *E. peplus* sap against prostate cancer cell lines, as compared to normal fibroblasts (NFF). PC-3 and DU145 are hormone resistant prostate cancer cell lines. LNcap is a hormone-sensitive prostate cancer cell line.

Compounds may be referred to in the subject specification by a compound code. These are defined in Table 1 below:

TABLE 1

| COMPOUND CODE | DESCRIPTION |
| --- | --- |
| PEP001 | Crude sap |
| PEP002 | Methanol and ether extract of *E. peplus* sap prepared according to Example 7 of PCT/AU98/00656 |
| PEP003 | Ingenane enriched fraction prepared according to Examples 2 and 4 |
| PEP004 | Jatrophane/Pepluane enriched fraction prepared according to Example 7 of PCT/AU98/00656 |
| PEP005 | Ingenol-3-angelate |
| PEP006 | 20-deoxy-Ingenol-3-angelate |
| PEP008 | 20-O-acetyl-ingenol-3-angelate |
| PEP009 | Acetone Extract of XAD (water extract) prepared according to Example 2 |
| PEP010 | Ingenane enriched fraction prepared according to Examples 3 and 4 |

DETAILED DESCRIPTION OF THE PREFERRED EMBODIMENTS

The present invention is predicated in part on the identification of biologically useful properties of chemical agents and chemical fractions comprising these agents obtainable from a member of the Euphorbiaceae family of plants or their botanical or horticultural relatives. These biologically useful properties include their use in the prophylaxis and/or treatment of prostate cancer including facilitating potentiation of the immune system or of cells or other components of the immune system in the treatment or amelioration of symptoms associated with prostate cancer.

Reference to "prostate cancer" includes cancers related thereto such as at the biochemical, physiological, pharmacological and immunological levels. Examples of related cancers include prostatic carcinogenesis, benign prostatic hyperplasia, prostatic intraepithelial carcinoma, carcinoma of the bladder, adenocarcinoma of the prostate and renal cell carcinoma. The term "prostate cancer" includes a condition having the characteristics of prostate cancer and includes conditions associated with cancers related to prostate cancer.

The term "treatment" is used in its broadest sense and includes the prevention of a disease condition as well as facilitating the amelioration of the effects of symptoms of prostate cancer or a related condition.

The term "prophylaxis" is also used herein in its broadest sense to encompass a reduction in the risk of development of prostate cancer. In certain conditions, an agent may act to treat a subject prophylactically. Furthermore, the prophylactic administration of an agent may result in the agent becoming involved in the treatment of a disease condition. Use of the terms "treatment" or "prophylaxis" is not to be taken as limiting the intended result which is to reduce the adverse effects of prostate cancer or to potentiate the immune system or components therein to ameliorate the symptoms or risk of development of symptoms caused or facilitated by prostate cancer.

The present invention is particularly directed to the use of one or more diterpenes from a member of the Euphorbiaceae family of plants or botanical or horticultural relatives of such plants. Reference herein to a member of the Euphorbiaceae family includes reference to species from the genera *Acalypha, Acidoton, Actinostemon, Adelia, Adenocline, Adenocrepis, Adenophaedra, Adisca, Agrostistachys, Alchornea, Alchorneopsis, Alcinaeanthus, Alcoceria, Aleturites, Amanoa, Andrachne, Angostyles, Anisophyllum, Antidesma, Aphora, Aporosa, Aporosella, Argythamnia, Astrococcus, Astrogyne, Baccanrea, Baliospermum, Bernardia, Beyeriopsis, Bischofia, Blachia, Blumeodondron, Bonania, Bradleia, Breynia, Breyniopsis, Briedelia, Buraeavia, Caperonia, Caryodendron, Celianella, Cephalocroton, Chaenotheca, Chaetocarpus, Chamaesyce, Cheilosa, Chiropetalumn, Choriophyllum, Cicca, Chaoxylon, Cleidon, Cleistanthus, Cluytia, Cnesmone, Cnidoscolus, Coccoceras, Codiaeum, Coelodiscus, Conami, Conceveiba, Conceveibastrum, Conceveïbum, Corythea, Croizatia, Croton, Crotonopsis, Crozophora, Cubanthus, Cunuria, Dactylostemon, Dalechampia, Dendrocousinsia, Diaspersus, Didymocistus, Dimorphocalyx, Discocarpus, Ditaxis, Dodecastingmna, Drypetes, Dysopsis, Elateriospermum, Endadenium, Endospermum, Erismanthus, Erythrocarpus, Erythrochilus, Eumecanthus, Euphorbia, Euphorbiodendron, Excoecaria, Flueggea, Calearia, Garcia, Gavarretia, Gelonium, Giara, Givotia, Glochidion, Clochidionopsis, Glycydendron, Gymnanthes, Gymnosparia, Haematospermum, Hendecandra, Hevea, Hieronima, Hieronyma, Hippocrepandra, Homalanthus, Hymenocardia, Janipha, Jatropha, Julocroton, Lasiocroton, Leiocarpus, Leonardia, Lepidanthus, Leucocroton, Mabea, Macaranga, Mallotus, Manihot, Mappa, Maprounea, Melanthesa, Mercurialis, Mettenia, Micrandia, Microdesmis, Microelus, Microstachy, Maocroton, Monadenium, Mozinna, Neoscortechinia, Omalanthus, Omphalea, Ophellantha, Orbicularia, Ostodes, Oxydectes, Palenga, Pantadenia, Paradrypeptes, Pausandra, Pedilanthus, Pera, Peridium, Petalostigma, Phyllanthus, Picrodendro, Pierardia, Pilinophytum, Pimeleodendron, Piranhea, Platygyna, Plukenetia, Podocalyx, Poinsettia, Poraresia, Prosartema, Pseudanthus, Pycnocoma, Quadrasia, Reverchonia, Richeria, Richeriella, Ricinella, Ricinocarpus, Rottlera, Sagotia, Sanwithia, Sapium, Savia, Sclerocroton, Sebastiana, Securinega, Senefeldera, Senefilderopsis, Serophyton, Siphonia, Spathiostemon, Spixia, Stillingia, Strophioblachia, Synadenium, Tetracoccus, Tetraplandra, Tetrochidium, Thyrsanthera, Tithymalus, Trageia, Trewia, Trigonostemon, Tyria* and *Xylophylla*.

The most preferred genus and most suitable for the practice of the present invention is the genus *Euphorbia*. Particularly useful species of this genus include *Euphorbia aaron-rossii, Euphorbia abbreviata, Euphorbia acuta, Euphorbia alatocaulis, Euphorbia albicaulis, Euphorbia algomarginata, Euphorbia aliceae, Euphorbia alta, Euphorbia anacampseros, Euphorbia andromedae, Euphorbia angusta, Euphorbia anthonyi, Euphorbia antiguensis, Euphorbia apocynifolia, Euphorbia arabica, Euphorbia ariensis, Euphorbia arizonica, Euphorbia arkansana, Euphorbia arteagae, Euphorbia arundelana, Euphorbia astroites, Euphorbia atrococca, Euphorbia baselicis, Euphorbia batabanensis, Euphorbia bergeri, Euphorbia bermudiana, Euphorbia bicolor, Euphorbia biformis, Euphorbia bifurcata, Euphorbia bilobata, Euphorbia biramensis, Euphorbia biuncialis, Euphorbia blepharostipula, Euphorbia blodgetti, Euphorbia boerhaavioides, Euphorbia boliviana, Euphorbia bracei, Euphorbia brachiata, Euphorbia brachycera, Euphorbia brandegee, Euphorbia brittonii, Euphorbia caesia, Euphorbia calcicola, Euphorbia campestris, Euphorbia candelabrum, Euphorbia capitellata, Euphorbia carmenensis, Euphorbia carunculata, Euphorbia cayensis, Euphorbia celastroides, Euphorbia chalicophila, Euphorbia chamaerrhodos, Euphorbia chamaesula, Euphorbia chiapensis, Euphorbia chiogenoides, Euphorbia cinerascens, Euphorbia clarionensis, Euphorbia colimae, Euphorbia colorata, Euphorbia commutata, Euphorbia consoquitlae, Euphorbia convolvuloides, Euphorbia corallifera, Euphorbia creberrima, Euphorbia crenulata, Euphorbia cubensis, Euphorbia cuspidata, Euphorbia cymbiformis, Euphorbia darlingtonii, Euphorbia defoliata, Euphorbia degeneri, Euphorbia deltoidea, Euphorbia dentata, Euphorbia depressa Euphorbia dictyosperma, Euphorbia dictyosperma, Euphorbia dioeca, Euphorbia discoidalis,*

*Euphorbia dorsiventralis, Euphorbia drumondii, Euphorbia duclouxii, Euphorbia dussii, Euphorbia eanophylla, Euphorbia eggersii, Euphorbia eglandulosa, Euphorbia elata, Euphorbia enalla, Euphorbia eriogonoides, Euphorbia eriophylla, Euphorbia esculaeformis, Euphorbia espirituensis, Euphorbia esula, Euphorbia excisa, Euphorbia exclusa, Euphorbia exstipitata, Euphorbia exstipulata, Euphorbia fendleri, Euphorbia filicaulis, Euphorbia filiformis, Euphorbia florida, Euphorbia fruticulosa, Euphorbia garber, Euphorbia gaumerii, Euphorbia gerardiana, Euphorbia geyeri, Euphorbia glyptosperma, Euphorbia gorgonis, Euphorbia gracilior, Euphorbia gracillima, Euphorbia gradyi, Euphorbia graminea, Euphorbia graminiea Euphorbia grisea, Euphorbia guadalajarana, Euphorbia guanarensis, Euphorbia gymnadenia, Euphorbia haematantha, Euphorbia hedyotoides, Euphorbia heldtichii, Euphorbia helenae, Euphorbia helleri, Euphorbia helwigii, Euphorbia henricksonii, Euphorbia heterophylla, Euphorbia hexagona, Euphorbia hexagonoides, Euphorbia hinkleyorum, Euphorbia hintonii, Euphorbia hirtula, Euphorbia hirta, Euphorbia hooveri, Euphorbia humistrata, Euphorbia hypericifolia, Euphorbia inundata, Euphorbia involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia latericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinisulicola, Euphorbia longipila, Euphorbia lupulina, Euphorbia lurida, Euphorbia lycioides, Euphorbia macropodoides, macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia microcephala, Euphorbia microclada, Euphorbia micromera, Euphorbia misella, Euphorbia missurica, Euphorbia montana, Euphorbia montereyana, Euphorbia multicaulis, Euphorbia multiforimis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidenztalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia paralias, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robutsta, Euphorbia romosa, Euphorbia rubida, Euphorbia rubrosperma, Euphorbia rupicola, Euphorbia sanmartensis, Euphorbia saxatilis M. Bieb, Euphorbia schizoloba, Euphorbia sclerocyathium, Euphorbia scopulorum, Euphorbia senilis, Euphorbia serpyllifolia, Euphorbia serrula, Euphorbia setiloba Engelm, Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammmilaris, Euphorbia subpeltata, Euphorbia subpubens, Euphorbia subreniforme, Euphorbia subtrifoliana, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaninowii, Euphorbia umbellulata, Euphorbia undulata, Euphorbia vermiformiis, Euphorbia versicolor, Euphorbia villifera, Euphorbia violacea, Euphorbia whitei, Euphorbia xanti* Engelm, *Euphorbia xylopoda* Greenmn., *Euphorbia yayalesia* Urb., *Euphorbia yungasensis, Euphorbia zeravschanica* and *Euphorbia zinniiflora.*

Particularly preferred species of the genus *Synadenium* include *Synadenium grantii* and *Synadenium compactum.*

Particularly preferred species of the genus *Monadenium* include *Monadenium lugardae* and *Monadenium guentheri.*

A preferred species of the genus *Endadenium* is *Endadenium gossweileni.*

*Euphorbia peplus* is particularly useful and is preferred in the practice of the present invention. Reference herein to "*Euphorbia peplus*" or its abbreviation "*E. peplus*" includes various varieties, strains, lines, hybrids or derivatives of this plant as well as its botanical or horticultural relatives. Furthermore, the present invention may be practiced using a whole Euphorbiaceae plant or parts thereof including sap or seeds or other reproductive material may be used. Generally, for seeds or reproductive material to be used, a plant or plantlet is first required to be propagated.

Reference herein to a Euphorbiaceae plant, a *Euphorbia* species or *E. peplus* further encompasses genetically modified plants. Genetically modified plants include transgenic plants or plants in which a trait has been removed or where an endogenous gene sequence has been down-regulated, up-regulated, mutated or otherwise altered including the alteration or introduction of genetic material which exhibits a regulatory effect on a particular gene. Consequently, a plant which exhibits a character not naturally present in a Euphorbiaceae plant or a species of *Euphorbia* or in *E. peplus* is nevertheless encompassed by the present invention and is included within the scope of the above-mentioned terms. Furthermore, the present invention contemplates hybrid plant cells or plants comprising hybrid plant cells formed by the fusion of two or more plant cells from different strains, species or genera and optionally regenerating a plant therefrom. Such hybrid plant cells are proposed to generate novel secondary metabolites having useful therapeutic properties.

The diterpenes are generally in extracts of the Euphorbiaceae plants. An extract may comprise, therefore, sap or liquid or semi-liquid material exuded from, or present in, leaves, stem, flowers, seeds and bark or between the bark and the stem. Most preferably, the extract is from sap. Furthermore, the extract may comprise liquid or semi-liquid material located in fractions extracted from sap, leaves, stems, flowers, bark or other plant material of the Euphorbiaceae plant. For example, plant material may be subject to physical manipulation to disrupt plant fibres and extracellular matrix material and inter- and intra-tissue extracted into a solvent including an aqueous environment. The fractions may include aqueous or alcohol extracts. Other extraction media are also contemplated including fractions prepared by BPLC or other fractionation systems. All such sources of the diterpenes are encompassed by the present invention including diterpenes obtained by synthetic routes.

The preferred diterpenes are selected from compounds of the ingenane, pepluane and jatrophane families. A compound is stated to be a member of the ingenane, pepluane or jatrophane families on the basis of chemical structure and/or chemical or physical properties. A compound which is a derivative of an ingenane, pepluane or jatrophane is nevertheless encompassed by the present invention through use of the terms "ingenane", "pepluane" or "jatrophane" since these terms include derivatives, chemical analogs and chemically synthetic forms of these families of compounds. One particularly preferred derivative is an angeloyl-substituted derivative of ingenane.

The chemical agents of the present invention may be in purified or isolated form meaning that the preparation is substantially devoid of other compounds or contaminating agents other than diluent, solvent or carrier or isoforms of the agents. Furthermore, the term "chemical agent" includes preparations of two or more compounds either admixed together or co-purified from a particular source. The chemical agent may also be a chemical fraction, extract or other preparation including sap from the Euphorbiaceae plant. The chemical agents or extracts or fractions of the present invention may also be referred to as "drugs" or "actives" or "active ingredients". The term "agent" is not to imply a synthetic compound and may include a fraction obtainable from the sap of the Euphorbiaceae plant. The term "obtainable" also includes "obtained".

Consequently, reference herein to a "chemical agent" includes a purified form of one or more compounds or a chemical fraction or extract such as from the sap of a Euphorbiaceae plant, and in particular a species of *Euphorbia*, and most preferably from *E. peplus* or botanical or horticultural relatives or variants thereof.

Accordingly, one aspect of the present invention contemplates a method for the treatment or prophylaxis of prostate cancer or a related cancer or -condition, said method comprising the administration to said subject of a symptom-ameliorating effective amount of a chemical agent obtainable from a plant of the Euphorbiaceae family or a derivative or chemical analog thereof which chemical agent is a diterpene selected from compounds of the ingenane, pepluane and jatrophane families and which chemical agent or derivative or chemical analog is represented by any one of the general formulae (I)-(V)

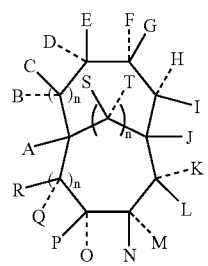

I wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

A-T are independently selected from hydrogen, $R_1$, $R_2$, $R_3$, F, Cl, Br, I, CN, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$, $(C=X)R_3$ or $X(C=X)R_3$ where X is selected from sulfur, oxygen and nitrogen;

$R_1$ and $R_2$ are each independently selected from $C_1$-$C_{20}$ alkyl (branched and/or straight chained), $C_1$-$C_{20}$ aralkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$]alkyl;

$R_3$ is selected from $R_1$, $R_2$, CN, $COR_1$, $CO_2R_1$, $OR_1$, $SR_1$, $NR_1R_2$, $N(=O)_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R)_2$;

A connected to B (or f, D (or E, R (or Q), P (or Q) or S (or D is a selection of $C_1$-$C_8$ disubstituted (fused) saturated or unsaturated carbocyclic or heterocyclic rings further substituted by $R_3$, $(C=X)R_3$ and $X(C=X)R_3$, including epoxides and thioepoxides;

J connected to I (or H), G (or F), K (or L), M (or N) or S (or T) is a selection of $C_1$-$C_8$ disubstituted (fused) saturated and unsaturated carbocyclic or heterocyclic rings further substituted by $R_3$, $(C=X)R_3$ and $X(C=X)R_3$, including epoxides and thioepoxides;

D (or E) connected to B (or C) or G (or F); I (or H) connected to G (or F); P (or O) connected to R (or Q) or M (or N); K (or L connected to N (or M) is a selection of $C_1$-$C_8$ disubstituted (fused) saturated or unsaturated carbocyclic or heterocyclic rings substituted by $R_3$, $(C=X)R_3$ and $X(C=X)R_3$, including epoxides and thioepoxides;

B and C, D and E, R and Q, P and Q, I and H, G and F K and L M and N or S and T are =X where X is selected from sulfur, oxygen, nitrogen, $NR_1R_2$, and $=CR_1R_2$

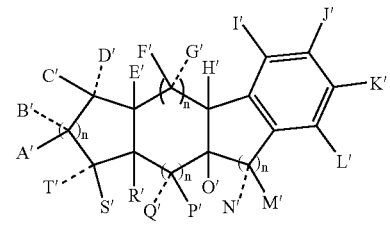

II wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

A'-T' are independently selected from hydrogen, $R_4$, $R_5$, $R_6$, F, Cl, Br, I, CN, $COR_4$, $CO_2R_4$, $OR_4$, $SR_4$, $NR_4R_5$, $CONR_4R_5$, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$, $(C=X)R_6$ or $X(C=X)R_6$ where X is selected from sulfur, oxygen and nitrogen;

$R_4$ and $R_5$ are each independently selected from $C_1$-$C_{20}$ alkyl (branched and/or straight chained), $C_1$-$C_{20}$ aralkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroaryllalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_4$, $SR_4$, N 5, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$]alkyl;

$R_6$ is selected from $R_4$, $R_5$, CN, $COR_4$, $CO_2R_4$, $OR_4$, $SR_4$, $NR_4R_5$, $N(=O)_2$, $NR_4OR_5$, $ONR_4R_5$, $SOR_4$, $SO_2R_4$, $SO_3R_4$, $SONR_4R_5$, $SO_2NR_4R_5$, $SO_3NR_4R_5$, $P(R_4)_3$, $P(=O)(R_4)_3$, $Si(R_4)_3$, $B(R_4)_2$;

E' and R' or H' and O' is a $C_2$-$C_8$ saturated or unsaturated carbocyclic or heterocyclic ring system further substituted by $R_6$, including epoxides and thiioepoxides;

O' connected to M' (or N') or O' (or E'); R' connected to Q' (or P') or S' (or T'); S' (or T') connected to A' (or B'); A' (or B') connected to C' (or D'); E' connected to C' (or D') or F' (or G'); H' connected to I'; I' connected to J'; J' connected to K'; K' connected to L'; L' connected to M' (or N') are $C_1$-$C_8$ disubstituted (fused) saturated or unsaturated carbocyclic or heterocyclic ring systems further substituted by $R_6$, $(C=X)R_6$ and $X(C=X)R$, including epoxides and thioepoxides;

A', B' and C', D' and F', G' and M', N' and P', Q' and S', T' are =X where X is selected from sulfur, oxygen, nitrogen, $NR_4R_5$, $(C=X)R_6$, $X(C=X)R_6$, and $=CR_7R_8$; $R_7$ and $R_8$ are each independently selected from $R_6$, $(C=X)R_6$ and $X(C=X)R_6$

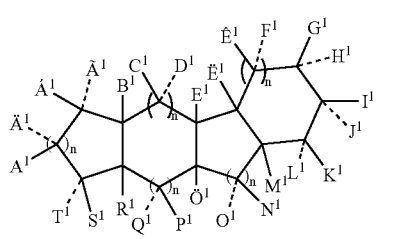

III $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$;

$B^1$ and $R^1$, $E^1$ and $Ö^1$ and $Ë^1$ and $M^1$ are selected from a $C_2$-$C_8$ saturated or unsaturated carbocyclic or heterocyclic ring system further substituted by $R_{11}$, including epoxides and thioepoxides;

$A^1$ (or $Ä^1$) connected to $Á^1$ (or $Ã^1$) or $T^1$ (or $S^1$); $B^1$ connected to $Á^1$ (or $Ã^1$) or $C^1$ (or $D^1$). $E^1$ connected to $Ë^1$ or $C^1$ (or $D^1$); $Ë^1$ connected to $É^1$ (or $F^1$); $G^1$ (or $H^1$) connected to $É^1$ (or $F^1$) or $I^1$ (or $J^1$); $K^1$ (or $L^1$) connected to $I^1$ (or $J^1$) or $M^1$; $M^1$ connected to $O^1$ (or $N^1$); $Ö^1$ connected $O^1$ (or $N^1$) or $P^1$ (or $Q^1$); $R^1$ connected $P^1$ (or $Q^1$) or $S^1$ (or $T^1$) are $C_1$-$C_8$ disubstituted (fused) saturated or unsaturated carbocyclic or heterocyclic ring systems further substituted by $R_{11}$, $(C=X)R_{11}$ and $X(C=X)R_{11}$, including epoxides and thioepoxides;

$A^1$, $Ä$ and $Á$, $Ã$ and $C^1$, $D^1$ and $F^1$, $É$ and $G^1$, $H^1$ and $I^1$, $J^1$ and $K^1$, $L^1$ and $N^1$, $O^1$ and $P^1$, $Q^1$ and $S^1$, $T^1$ are =X where X is selected from sulfur, oxygen, nitrogen, $NR_9R_{10}$, including $(C=X)R_{11}$ and $X(C=X)R_{11}$, and $=CR_{12}R_{13}$;

$R_{12}$ and $R_{13}$ are independently selected from $R_{11}$, $(C=X)R_{11}$ and $X(C=X)R_{11}$

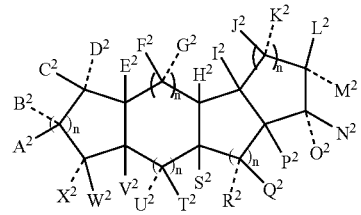

IV wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^1$-$T^1$ are independently selected from hydrogen, $R_9$, $R_{10}$, $R_{11}$, F, Cl, Br, I, CN, $OR_9$, $SR_9$, $NR_9R_{10}$, $N(=O)_2$, $NR_9OR_{10}$, $ONR_9R_{10}$, $SOR_9$, $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$, $(C=X)R_{11}$, or $X(C=X)R_{11}$, where X is selected from sulfur, oxygen and nitrogen;

$R_9$ and $R_{10}$ are each independently selected from $C_1$-$C_{20}$ alkyl (branched and straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and straight chained), $C_2$-$C_{10}$ alkynyl (branched and straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_9$, $SR_9$, $NR_9R_{10}$, $N(=O)_2$, $NR_9OR_{10}$, $ONR_9R_{10}$, $SOR_9$, $SO_2R_9$, $SO_3R_9$, $SONR_9R_{10}$, $SO_2NR_9R_{10}$, $SO_3NR_9R_{10}$, $P(R_9)_3$, $P(=O)(R_9)_3$, $Si(R_9)_3$, $B(R_9)_2$]alkyl;

$R_{11}$ is selected from $R_9$, $R_{10}$, CN, $COR_9$, $CO_2R_9$, $OR_9$, $SR_9$, $NR_9R_{10}$, $N(=O)_2$, $NR_9OR_{10}$, $ONR_9R_{10}$, $SOR_9$, wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^2$-$X^2$ are independently selected from hydrogen, $R_{14}$, $R_{15}$, $R_{16}$, F, Cl, Br, I, CN, $OR_{14}$, $SR_{14}$, $NR_{14}R_{15}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, $B(R_{14})$, $(C=Y)R_{16}$ or $Y(C=Y)R_{16}$ where Y is selected from sulfur, oxygen and nitrogen;

$R_{14}$ and $R_{15}$ are each independently selected from $C_1$-$C_{20}$ alkyl (branched and/or straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{14}$, $SR_{14}$, $NR_{14}R_{10}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, B$(R_{14})_2$]alkyl;

$R_{16}$ is selected from $R_{14}$, $R_{15}$, CN, $COR_{14}$, $CO_2R_{15}$, $OR_{14}$, $SR_{14}$, $NR_{14}R_{15}$, $N(=O)_2$, $NR_{14}OR_{15}$, $ONR_{14}R_{15}$, $SOR_{14}$, $SO_2R_{14}$, $SO_3R_{14}$, $SONR_{14}R_{15}$, $SO_2NR_{14}R_{15}$, $SO_3NR_{14}R_{15}$, $P(R_{14})_3$, $P(=O)(R_{14})_3$, $Si(R_{14})_3$, $B(R_{14})_2$;

$E^2$ and $V^2$, $H^2$ and $S^2$, and $I^2$ and $P^2$ are $C_2$-$C_8$ saturated or unsaturated carbocyclic or heterocyclic ring system further substituted by $R_{16}$, including epoxides and thioepoxides;

$A^2$ (or $B^2$) connected to $C^2$ (or $D^2$) or $W^2$ (or $X^2$); $E^2$ connected to $C^2$ (or $D^2$) or $F^2$ (or $G^2$); $H^2$ connected to $F^2$ (or $G^2$) or $I^2$; $I^2$ connected to $J^2$ (or $K^2$); $L^2$ (or $M^2$) connected to $J^2$ (or $K^2$) or $N^2$ (or $O^2$); $R_2$ (or $Q^2$) connected to $P^2$ or $S^2$; $V^2$ connected to $U^2$ (or $T^2$) or $W^2$ (or $X^2$) are $C_1$-$C_8$ disubstituted (fused) saturated or unsaturated carbocyclic or heterocyclic ring systems further substituted by $R_{16}$, (C=Y)$R_{16}$ and Y(C=Y)$R_{16}$, including epoxides and thioepoxides;

$A^2$, $B^2$; $C^2$; $D^2$; $F^2$, $G^2$; $J^2$, $K^2$; $L^2$, $M^2$; $N^2$, $O^2$; $Q^2$, $R^2$; $U^2$, $T^2$ and $X^2$, $W^2$ are =Y where Y is selected from sulfur, oxygen, nitrogen, $NR_{14}R_{15}$ and =$CR_{17}R_{18}$;

$R_{17}$ and $R_{18}$ are independently selected from $R_{16}$, (C=Y)$R_{16}$ and Y(C=Y)$R_{16}$

V

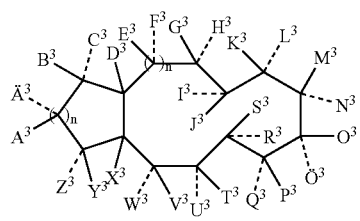

wherein:
n is 0-10 atoms selected from carbon, oxygen, nitrogen, sulfur, phosphorus, silicon, boron, arsenic and selenium, wherein the ring defined by said atoms is saturated or unsaturated, including epoxides and thioepoxides;

$A^3$-$Z^3$ are independently selected from hydrogen, $R_{19}$, $R_{20}$, $R_{21}$, F, Cl, Br, I, CN, $OR_{19}$, $SR_{19}$, $NR_{19}R_{20}$, N(=O)$_2$, $NR_{19}OR_{20}$, $ONR_{19}R_{20}$, $SOR_{19}$, $SO_2R_{19}$, $SO_3R_{19}$, $SONR_{19}R_{20}$, $SO_2NR_{19}R_{20}$, $SO_3NR_{19}R_{20}$, $P(R_{19})_3$, $P(=O)(R_{19})_3$, $Si(R_{19})_3$, $B(R_{19})_2$, (C=Ø)$R_{21}$ or Ø(C=Ø)$R_{21}$ where Ø is sulfur, oxygen and nitrogen;

$R_{19}$ and $R_{20}$ are each independently selected from $C_1$-$C_{20}$ alkyl (branched and/or straight chained), $C_1$-$C_{20}$ aralkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{19}$, $SR_{19}$, $NR_{19}R_{20}$, N(=O)$_2$, $NR_{19}OR_{20}$, $ONR_{19}R_{20}$, $SOR_{19}$, $SO_2R_{19}$, $SO_3R_{19}$, $SONR_{19}R_{20}$, $SO_2NR_{19}R_{20}$, $SO_3NR_{19}R_{20}$, $P(R_{19})_3$, $P(=O)(R_{19})_3$, $Si(R_{19})_3$, B($R_{19}$)$_2$]alkyl;

$R_{21}$ is selected from $R_{19}$, $R_{20}$, CN, $COR_{19}$, $CO_2R_{19}$, $OR_{19}$, $SR_{19}$, $NR_{19}R_{20}$, N(=O)$_2$, $NR_{19}OR_{20}$, $ONR_{19}R_{20}$, $SOR_{19}$, $SO_2R_{19}$, $SO_3R_{19}$, $SONR_{19}R_{20}$, $SO_2NR_{19}R_{20}$, $SO_3NR_{19}R_{20}$, $P(R_{19})_3$, $P(=O)(R_{19})_3$, $Si(R_{19})_3$, $B(R_{19})_2$;

$D^3$ connected to $X^3$ is a $C_2$-$C_8$ saturated or unsaturated carbocyclic or heterocyclic ring system further substituted by $R_{21}$, including epoxides and thioepoxides; $A^3$ (or $Ä^3$) connected to $B^3$ (or $C^3$) or $Z^3$ (or $Y^3$); $D^3$ connected to $B^3$ (or $C^3$) or $E^3$ (or $F^3$); $G^3$ (or $H^3$) connected to $E^3$ (or $F^3$) or $I^3$ (or $J^3$); $L^3$ (or $K^3$ connected to $I^3$ (or $J^3$) or $M^3$ (or $N^3$; $O^3$ (or $Ö^3$) connected to $N^3$ (or $M^3$) or $P^3$ (or $Q^3$). $S^3$ (or $R^3$) connected to $Q^3$ (or $P^3$) or $U^3$ (or $T^3$). $W^3$ (or $V^3$) connected to $U^3$ (or $T^3$) or $X^3$; $X^3$ connected to $Y^3$ (or $Z^3$) are $C_1$-$C_8$ disubstituted (fused) saturated or unsaturated carbocyclic or heterocyclic ring systems further substituted by $R_{21}$, (C=Ø) $R_{21}$ and Ø (C=Ø)$R_{21}$, including epoxides and thioepoxides;

$A^3$, $Ä^3$; $B^3$, $C^3$; $E^3$, $F^3$; $G^3$, $H^3$; $I^3$, $J^3$; $K^3$, $L^3$; $M^3$, $N^3$, $O^3$, $Ö^3$; $P^3$, $S^3$, $R^3$, $U^3$, $T^3$, $W^3$, $V^3$, and $Z^3$, $Y^3$ are =Ø where Ø is selected from sulfur, oxygen, nitrogen, $NR_{19}R_{20}$, and =$CR_{22}R_{23}$; and $R_{22}$ and $R_{23}$ are selected from $R_{21}$, (C=Ø)$R_{21}$ and Ø(C=Ø)$R_{21}$;

wherein said chemical agent or its derivatives or chemical analogs is administered for a time and under conditions sufficient to ameliorate one or more symptoms associated with said prostate cancer or a related condition.

More particularly, the present invention is directed to a method for the treatment or prophylaxis of prostate cancer or a related condition in an subject, said method comprising the administration to said subject of a symptom-ameliorating effective amount of a chemical agent obtainable from *E. peplus* or a derivative or chemical analog thereof which chemical agent is a diterpene selected from compounds of the ingenane, pepluane and jatrophane families and which chemical agent or derivative or chemical analog is represented by any one of the general formulae (I)-(V) as defined herein and wherein said chemical agent or its derivatives or chemical analogs is administered for a time and under conditions sufficient to ameliorate one or more symptoms associated with said prostate cancer.

In a related embodiment, the subject chemical agents may be used to increase the sensitivity of prostate cancer cells to the activity of the immune system or to chemical agents or otherwise be used to potentiate the immune system against prostate cancer cells. This method involves the administration to a subject of the chemical agents of the invention. In an alternative embodiment, the prostate cancer cells may be removed such as by biopsy, treated with the subject chemical agents and returned to the subject in order to induce a more potent immune response against the prostate cancer cells.

Accordingly, the present invention provides a method for immunopotentiation of a subject in the treatment and prophylaxis of said subject for prostate cancer or a related cancer or condition, said method comprising administration to said subject of a symptom-ameliorating effective amount of a diterpene, or a chemical fraction comprising same from a plant of the Euphorbiaceae or a derivative or chemical analog of said diterpene having the structures as defined herein, said administration being for a time and under conditions sufficient to potentiate components of the immune system against prostate cancer cells.

Especially preferred chemical agents or derivatives or chemical analogs thereof in the practice of the present invention are represented by the general formula (VI):—

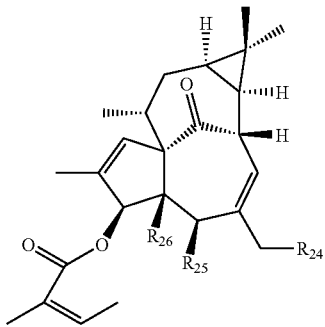

wherein:—

$R_{24}$, $R_{25}$ and $R_{26}$ are independently selected from hydrogen, $R_{27}$, $R_{28}$, F, Cl, Br, I, CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$, $(C=X)R_{29}$ or $X(C=X)R_{29}$ where X is selected from sulfur, oxygen and nitrogen;

$R_{27}$ and $R_{28}$ are each independently selected from $C_1$-$C_{20}$ alkyl (branched and/or straight chained), $C_1$-$C_{20}$ arylalkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ [CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$]alkyl;

$R_{29}$ is selected from $R_{27}$, $R_{28}$, CN, $COR_{27}$, $CO_2R_{27}$, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$.

In a preferred embodiment, $R_{24}$ is hydrogen, OAcetyl or OH.

In another preferred embodiment, $R_{25}$ is OH.

In another preferred embodiment, $R_{26}$ is OH.

As used herein, the term "alkyl" refers to linear or branched chains. The term "haloalkyl" refers to an alkyl group substituted by at least one halogen. Similarly, the term "haloalkoxy" refers to an alkoxy group substituted by at least one halogen. As used herein the term "halogen" refers to fluorine, chlorine, bromine and iodine.

As used herein the term "aryl" refers to aromatic carbocyclic ring systems such as phenyl or naphthyl, anthracenyl, especially phenyl. Suitably, aryl is $C_6$-$C_{14}$ with mono, di- and tri-substitution containing F, Cl, Br, I, $NO_2$, $CF_3$, CN, $OR_1$, $COR_1$, $CO_2R_1$, $NHR_1$, $NR_1R_2$, $NR_1OR_2$, $ONR_1R_2$, $SOR_1$, $SO_2R_1$, $SO_3R_1$, $SONR_1R_2$, $SO_2NR_1R_2$, $SO_3NR_1R_2$, $P(R_1)_3$, $P(=O)(R_1)_3$, $Si(R_1)_3$, $B(R_1)_2$, wherein $R_1$ and $R_2$ are defined above As used herein the terms "heterocycle", "heterocyclic", "heterocyclic systems" and the like refer to a saturated, unsaturated, or aromatic carbocyclic group having a single ring, multiple fused rings (for example, bicyclic, tricyclic or other similar bridged ring systems or substituents), or multiple condensed rings, and having at least one heteroatom such as nitrogen, oxygen, or sulfur within at least one of the rings. This term also includes "heteroaryl" which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring, which is either completely, or partially, saturated. Suitable heteroaryl moieties include, but are not limited to oxazolyl, thiazaoyl, thienyl, furyl, 1-isobenzofuranyl, 3H-pyrrolyl, 2H-pyrrolyl, N-pyrrolyl, imidazolyl, pyrazolyl, isothiazolyl, isooxazolyl, pyridyl, pyrazinyl, pyrinidinyl, pyradazinyl, indolizinyl, isoindolyl, indoyl, indolyl, purinyl, phthalazinyl, 1,2,3-triazolyl, 1,2,4-triazolyl, 1,2,3-oxadiazoyl, 1,2,4-oxadiazolyl, 1,2,5-oxadiazolyl, 1,3,4-oxadiazolyl, 1,2,3,4-oxatriazolyl, 1,2,3,5-oxatriazolyl, 1,3,5-triazinyl, 1,2,4-triazinyl, 1,2,3-triazinyl, azepinyl, oxepinyl, thiepinyl, benzofuranyl, isobenzofuranyl, thionaphthenyl, isothionaphthenyl, indoleninyl, 2-isobenzazolyl, 1,5-pyrindinyl, pyrano[3,4b]pyrrolyl, isoindazolyl, indoxazinyl, benzoxazolyl, anthranilyl, quinolinyl, isoquinolinyl, cinnolinyl, quinazolinyl, naphthyridinyl, pyrido[3,4-b]pyridinyl, and pyrido[3,2-b]pyridinyl, pyrido[4,3-b]pyridinyl.

Particularly useful compounds in accordance with the present invention include 5,8,9,10,14-pentaacetoxy-3-benzoyloxy-15-hydroxypepluane (pepluane), derivatives of said pepluane, jatrophanes of Conformation II including 2,3,5,7,15-pentaacetoxy-9-nicotinoyloxy-14-oxojatropha-6(17), 11E-diene (jatrophane 1), derivatives of said jatrophane 1,2,5,7,8,9,14-hexaacetoxy-3-benzoyloxy-15-hydroxy-jatropha-6(17), 11E-diene (jatrophane 2), derivatives of said jatrophane 2,2,5,14-triacetoxy-3-benzoyloxy-8,15-dihydroxy-7-isobutyroyloxy-9-nicotinoyloxy-jatropha-6(17), 11E-diene (jatrophane 3), derivatives of said jatrophane 3,2,5,9,14-tetraacetoxy-3-benzoyloxy-8,15-dihydroxy-7-isobutyroyloxyjatropha-6(17),11E-diene) (jatrophane 4), derivatives of said jatrophane 4,2,5,7,14-tetraacetoxy-3-benzoyloxy-8,15-dihydroxy-9-nicotinoyloxyjatropha-6(17), 11E-diene (jatrophane 5), derivatives of said jatrophane 5,2,5,7,9,14-pentaacetoxy-3-benzoyloxy-8,15-dihydroxyjatropha-6(17),11E-diene (jatrophane 6), derivatives of said jatrophane 6, or pharmaceutically acceptable salts of these.

Even more particularly preferred compounds are angeloyl substituted ingenanes or derivatives thereof such as ingenol-3-angelate, 20-deoxy-ingenol-3-angelate, 20-O-acetyl-ingenol-3-angelate, or derivatives of said angelates, or pharmaceutically acceptable salts of these.

The present invention extends to all functional jatrophane or pepluane derivatives. For example, such derivatives include acetyl derivatives (e.g. jatrophane 4 with an acetylation of the 8-hydroxyl group), deacytlated derivatives (e.g. jatrophane 1 with a deacetylation of the 2-hydroxy group). Pepluane derivatives as described by Hohmann et al. (1999) or with a hydroxylation of the 10-hydroxy group and all of the compounds described in International Patent Application No. PCT/AU98/00656, International Patent Application No. PCT/AU/000678, International Patent Application No. PCT/AU01/00679 and International Patent Application No. PCT/AU01/00680 are also within the scope of the present invention. Other exemplary derivatives contemplated by the present invention include angeloyl derivatives of jatrophanes and pepluanes, tiglic acid derivatives and derivatives comprising the trans-isomer of angelic acid. Derivatives or analogs of the compounds also include alterations which change the hydrophilicity or hydrophobicity of the molecule so as to improve its transport in a biological system are also encompassed within this scope. Suitable modifications can readily be effected and tested using methods known in the art. Whilst not intending to limit the invention to any proposed mechanism or action, it is proposed that activation can lead to down-regulation of protein kinase C (PKC) via the rapid destruction of activated enzyme and thus the beneficial effect may be due to the ultimate down-regulation of PKC activity or of PKC-mediated signalling in addition to direct killing of prostate cancer cells. Furthermore, again not wishing to limit the present invention to any one theory or mode of action, it is possible that a sum or all of the chemical agents of the invention mediate effects against cancer cells via activation of inflammatory cells and/or by the induction of cytokines and/or chemokines.

Accordingly, a particularly preferred embodiment of the present invention contemplates a method for the treatment or prophylaxis of a subject with prostate cancer or a related cancer or condition or with the symptoms of prostate cancer, said method comprising the administration to said subject of a symptom-ameliorating effective amount of an angeloyl-substituted ingenane or a chemical fraction or plant extract comprising same.

Even more preferably, the present invention provides a method for the treatment or prophylaxis of a subject with prostate cancer or a related cancer or condition or with the symptoms of prostate cancer, said method comprising the administration to said subject of a symptom-ameliorating effective amount of one or more of ingenol-3-angelate, 20-deoxy-ingenol-3-angelate and/or 20-O-acetyl-ingenol-3-angelate or a derivative thereof or a pharmaceutically acceptable salt of these or a chemical fraction or plant extract comprising same. Preferably, the derivative is selected from an ester derivative or an acetylated derivative.

The chemical agents of the present invention may be also optionally coupled to a targeting agent. This may suitably be a bone-seeking agent such as a bisphosphonate, in order to target the chemical agents to bone metastases or an antibody directed to a prostate-specific tumor marker such as prostate-specific antigen (PSA), prostate-specific membrane antigen (PSMA), PSA receptor or other prostate cancer antigen, in order to target the active compound to prostate cancer cells. A preferred bisphosphonate is methylene disphosphonate. Where an antibody is used, the antibody is preferably monoclonal and more preferably is a humanized or human monoclonal antibody. Antibodies may be specific not only to prostate-specific tumor markers but also to components of the immune system such as dendritic cells, B- or T-cells. Methods for making such monoclonal antibodies and suitable methods for coupling the active agent to the targeting agent are well known in the art.

Representative coupling methods for lining the chemical agents of the invention through covalent or non-covalent bonds to the targeting agent include chemical cross-linkers and heterobifunctional cross-linking compounds (i.e. "linkers") that react to form a bond between reactive groups (such as hydroxyl, amino, amido, or sulfhydryl groups) in a chemical agent and other reactive groups (of a similar nature) in the targeting agent. This bond may be, for example, a peptide bond, disulfide bond, thioester bond, amide bond, thioether bond and the like. In one illustrative example, conjugates of monoclonal antibodies with drugs have been summarized by Morgan and Foon (Monoclonal Antibody Therapy to Cancer: Preclinical Models and Investigations, Basic and Clinical Tumor Immunology, Vol. 2, Kluwer Academic Publishers, Hingham, Mass.) and by Uhr J. of Immunol. 133:i-vii, 1984). In another illustrative example where the conjugate contains a radionuclide cytostatic agent, U.S. Pat. No. 4,897,255 (Fritzberg et al.) is instructive of coupling methods that may be useful. In a preferred embodiment, the therapeutic conjugate contains a metastasis- or prostate cancer specific antigen-binding protein (e.g. monoclonal antibody) coupled covalently to a chemical agent of the invention. In this case, the covalent bond of the linkage may be formed between one or more amino, sulfhydryl, or carboxyl groups of the binding protein and (a) the chemical agent itself; (b) a carboxylic acid of the chemical agent; (c) an ester of the chemical agent; or (d) complexes of the chemical agent with poly-L-lysine or any polymeric carrier.

The choice of coupling method will be influenced by the choice of targeting agent and the chemical agent and also by such physical properties as, e.g. shelf life stability and/or by such biological properties as, e.g. half-life in cells and blood, intracellular compartmentalisation route and the like.

Reference herein to a subject includes a human, primate, livestock animal (e.g. sheep, cow, horse, pig, goat, donkey), laboratory test animal (e.g. mouse, rat, guinea pig, hamster) or companion animal (e.g. dog, cat). The above-mentioned animals may also be useful in animal models for prostate cancer and the use of the subject chemical agents in an animal model is considered useful in accordance with the present invention.

The preferred subject is a human or primate or laboratory test animal.

The most preferred subject is a human.

The present invention further contemplates the use of the subject chemical agents in combination with other therapeutic procedures used in the treatment of prostate cancer and/or in the amelioration of symptoms associated with prostate cancer.

Accordingly, another aspect of the present invention contemplates a method for the treatment or prophylaxis of prostate cancer or a related cancer or condition in a subject, said method comprising the simultaneous or sequential administration to said subject of a symptom-ameliorating effective amount of a chemical agent derived from a plant of the Euphorbiaceae family as hereinbefore described together with a therapeutic protocol or a symptom-ameliorating effective amount of another chemical agent or a physical agent.

For example, the subject chemical agents from Euphorbiaceae maybe used simultaneously with or sequentially to or otherwise in combination with chemotherapeutic agents. Such agents include the compounds gemicitabine, herceptin, irinotecan, leustatin navelbine, rituxan, ST1 571, taxotere, topotecan, xeloda, zometa vinblastine, vinorelbine, vinaesine, treosulfan, tomudex, thiotepa, thioquaunine, streptozocin, procabazine, mitomycin, methotrexate mercaptopurine, melphaan, lomustine, irinotecan, ipospamide, idarubicin, gemcitabine fludarabine, etoposide, epirubicin, doxorubicin, paunorubicin, dacarbazine, cytarabine, cyclophosphamide, cisplatin, chlorambucil, carmustine, carboplatin, busulphan, bleomycin, asparaginase, adriamycin, actinomycin P, mitoxanthrone, prednisone, taxol VP-16 and ketokonazole.

The present invention also provides for use of chemopreventive agents in combination with the chemical agents of the invention. Such chemopreventive agents include toremifene analogs or metabolites thereof which are well known to those skilled in the art. Other examples of cancer chemopreventive agents include 4-chloro-1,2-diphenyl-1-[4-[2-(N-methylamino)ethoxy]phenyl]-1-butene; 4-chloro-1,2-diphenyl-4-[4-[2-(N,N-1-diethyl-amino)ethoxy]phenyl]-1-butene; 4-chloro-1,2-diphenyl-1-14-(aminoethoxy) phenyl]-1-butene; 4-chloro-1-(4-hydroxyphenyl)-1-[4-[2-(N,N-dimethylamino)ethoxy]phenyl]-2-phenyl-1-butene; 4-chloro-1-(4-hydroxyphenyl)-1-[4-[2-(N-methylamino) ethoxy]phenyl]-2-phenyl-1-butene; and 4-chloro-1,2-bis(4-hydroxyphenyl)-1-[4-[2-(N,N-dimethyl-amino)ethoxy]phenyl]-1-butene.

"Sequential" treatment includes the administration of Euphorbiaceae compounds and the chemotherapeutic compounds in either order and within seconds, minutes, hours, days, weeks or months. "Simultaneous" treatment means the agents are administered substantially at the same time such as in the same preparation or the concurrent administration of each agent by separate routes.

Prostate cancer therapy may in addition or as an alternative involve hormone therapy. Such hormone therapy includes the administration of gonadotrophic-releasing hormones (GnRH) (also known as luteinizing hormone-releasing hormones (LHRH), lupron, zolodex, casodox, flutamide and estrogen or analogs thereof.

Another prostate cancer therapy contemplated for use in combination with the Euphorbiaceae compounds is immunotherapy. For example, monoclonal antibodies including human antibodies and humanized non-human antibodies directed to prostate cancer antigens may be administered. Alternatively, vaccine compositions directed to prostate cancer agents may be used. Examples of prostate cancer antigens include but are not limited to seminoprotein β-micro seminoprotein and isoforms and differentially acylated versions of isoforms and epitopes on fragments, carcinoembryonic antigen, chymotrypsin-like serine protease, members of the kallikrein family of proteins, prostate stem cell antigen and PSMA.

Still other therapies include exposure of the subjects or affected areas on subjects to physical agents. An example of a physical agent is radiation such as TV radiation, ionizing radiation or radioactive particles.

Furthermore, the administration of the above therapeutic agents or treatments may also accompany interventionist procedures such as surgery or biopsy.

In addition, prostate cancer therapy may also involve the reduction in expression of certain genes associated with prostate cancer such as metastatic sequences. Examples include the caveolin gene. Such genes or sequences may be down-regulated using, for example, antisense technology, sense suppression, co-suppression, ribozymes or molecules which induce RNAi specific for the genes or their transcripts. Alternatively, or in addition, an anti-caveolin antibody or antigen-binding fragment thereof may be administered.

The present invention further extends to pharmaceutical compositions useful in treating a subject presenting with prostate cancer or the symptoms of prostate cancer. In this regard, the chemical agents of the present invention can be used as actives for the treatment or prophylaxis of prostate cancer or a related condition in a subject. The chemical agents can be administered to a patient either by themselves, or in pharmaceutical compositions where they are mixed with a suitable pharmaceutically acceptable carrier alone or in combination with other compounds such as anti-cancer compounds.

Accordingly, the present invention also provides a composition for treatment and/or prophylaxis of prostate cancer or a related cancer or condition in a subject, comprising one or more chemical agents of the present invention, together with a pharmaceutically acceptable carrier and/or diluent, and optionally one or more other active compounds.

The term "composition" includes an agent or other formulation.

Depending on the specific conditions being treated, chemical agents may be formulated and administered systemically or locally. Topical and/or intralesional administration are particularly useful in the practice of the present invention. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. The agents may also be delivered at or near the site of the tumor by catheter delivery into blood vessels supplying the prostate. For injection, the chemical agents of the present invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intra-muscular and subcutaneous injection is appropriate, for example, for administration of immunomodulatory compositions and vaccines.

The chemical agents can be formulated readily using pharmaceutically acceptable carriers well known in the art into dosages suitable for oral administration. Such carriers enable the compounds of the invention to be formulated in dosage forms such as tablets, beads, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water. Slow release formulations are also contemplated by the present invention.

Formulations of active compounds in beads or other microparticles are particularly useful for topical or intralesional administration and are specifically encompassed by the present invention.

Pharmaceutical compositions suitable for use in the present invention include compositions wherein the active ingredients are contained in an effective amount to achieve their intended purpose. The dose of agent administered to a patient should be sufficient to effect a beneficial response in the patient over time such as a reduction in the symptoms associated with prostate cancer or related condition in a subject. The quantity of the agent(s) to be administered may depend on the subject to be treated inclusive of the age, sex, weight and general health condition thereof. In this regard, precise amounts of the agent(s) for administration will depend on the judgement of the practitioner. In determining the effective amount of the chemical agent to be administered in the treatment or prophylaxis of a condition associated with prostate cancer or related condition, the physician may evaluate progression of the disorder. In any event, those of skill in the art may readily determine suitable dosages of the chemical agents of the present invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as., for example, maize starch, wheat starch, rice starch, potato starch, gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in a manner that is itself known, e.g. by means of conventional mixing, dissolving, granulating, dragee-making, levigating, emulsifying, encapsulating, entrapping or lyophilising processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the chemical agents of the present invention may also include injecting or implanting controlled releasing devices designed specifically for this purpose or other forms of implants modified to act additionally in this fashion. Controlled release of an agent of the present invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres, for example Captisol® or hyaluronic acid. Encapsulation is preferred for permitting controlled release of the subject chemical agents. Preferred vehicles for encapsulation include but are not limited to the microspheres described, for example, by Kanellakopoulou et al. (2000), Jain et al. (1998) and Thomasin et al. (1998) and the liposomal deliver systems described, for example, by Gabizon (2001), Kunisawa et al. (2001), Muggia (2001) and Nishioka et al. (2001).

Chemical agents of the present invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any chemical agent used in the method of the present invention, the therapeutically effective dose can be estimated initially from cell culture assays such as to reduce the growth of prostate cancer cells in vitro. For example, a dose can be formulated in animal models to achieve a circulating concentration range that includes the IC50 as determined in cell culture (e.g. the concentration of a test agent, which achieves a half-maximal inhibition of cancer cells). Such information can be used to more accurately determine useful doses in humans.

Toxicity and therapeutic efficacy of such chemical agents can be determined by standard pharmaceutical procedures in cell cultures or experimental animals, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosages for use in humans. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition (see for example Fingl et al., 1975, in "The Pharmacological Basis of Therapeutics", Ch. 1 p1).

Dosage amount and interval may be adjusted individually to provide plasma levels of the active agent which are sufficient to maintain symptom-ameliorating effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the compound in a local rather than systemic manner, for example, via injection of the compound directly into a tissue, often in a depot or sustained release formulation. Furthermore, one may administer the drug in a targeted drug delivery system, for example, in a liposome coated with tissue-specific antibody. The liposomes will be targeted to and taken up selectively by the tissue. In cases of local administration or selective uptake, the effective local concentration of the agent may not be related to plasma concentration.

The chemical agents of the present invention can also be delivered topically. For topical administration, a composition containing between 0.001-5% or more chemical agent is generally suitable. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

In one embodiment, the topical Composition is administered topically to a subject, e.g. by the direct laying on or spreading of the composition on the epidermal or epithelial tissue of the subject, or transdermally via a "patch". Such compositions include, for example, lotions, creams, solutions, gels and solids. Suitable carriers for topical administration preferably remain in place on the skin as a continuous film, and resist being removed by perspiration or immersion in water. Generally, the carrier is organic in nature and capable of having dispersed or dissolved there a chemical agent of the present invention. The carrier may include pharmaceutically-acceptable emollients, emulsifiers, thickening agents, solvents and the like.

The present invention also features a process for separating diterpenes from a biomass containing same, said process comprising contacting the biomass with an aqueous solvent for a time and under conditions sufficient to extract the diterpenes into said solvent.

The aqueous solvent is preferably water.

Suitably, the biomass is derived from a plant, which is preferably a member of the Euphorbiaceae family of plants or botanical or horticultural relatives of such plants. Matter from the plant (e.g. foliage) stems, roots, seeds, bark, etc.) is preferably cut, macerated or mulched to increase the surface area of the plant matter for aqueous extraction of the diterpenes.

The process preferably further comprises adsorbing the diterpenes to a non-ionic adsorbent, which is suitably a non-ionic porous synthetic adsorbent. Among the non-ionic porous synthetic adsorbents that can be used for the purposes of the present invention include, but are not restricted to, aromatic copolymers mainly composed of styrene and divinylbenzene, and methacrylic copolymers mainly composed of monomethacrylate and dimethacrylate. Such non-ionic porous synthetic adsorbents which comprise, as the basic structure, aromatic copolymers mainly composed of styrene and divinylbenzene include, for example, Diaion HP10, HP20, HP21, HP30, HP40, HP50, SP850, and SP205 (trade names: Mitsubishi Chemical Corp.), and Amberlite XAD-2, XAD4, (trade names: Rohm and Haas Co.). Examples of non-ionic porous synthetic adsorbent which comprise, as the basic structure, methacrylic copolymer mainly composed of monomethacrylate and dimethacrylate are Diaion HP2MG, Amberlite XAD-7, XAD-8 and XAD-16 and others.

Preferably, the process further comprises eluting diterpenes from the non-ionic adsorbent with water and water-soluble organic solvent(s).

The treatment may be conducted by a batch method using water and water-soluble organic solvent(s) which dissolve diterpenes, or may also be conducted continuously or in batch using a column chromatography method.

Examples of a water-soluble organic solvent which may be used in the present invention are alcohols such as methanol, ethanol, n-propyl alcohol, isopropyl alcohol, and tert-butanol, ethers such as dioxane and tetrahydrofuran, ketones such as acetone, amides such as dimethylformamide, sulfur-containing compounds such as dimethylsulfoxide. Two or more of such organic solvents may be mixed for use. In addition, solvents less soluble in water, for example, alcohols such as n-butanol, esters such as methyl formate and methyl acetate, and ketones such as methyl ethyl ketone may also be used to the extent that it does not separate during development. Particularly preferred water-soluble organic solvents are alcohols, in particular, methanol, ethanol, propyl alcohol, and the like. Furthermore, different kinds of solvent may also be used sequentially for development.

Diterpenes can be further purified using media and techniques which separate compounds on the basis of molecular size and/or polarity. In a preferred embodiment of this type, the diterpenes are separated using Sephadex LH-20 resin and preferably using water and water-soluble organic solvent(s) for development.

The testing of the chemical agents of the present invention is conveniently conducted using in vivo animal models for prostate cancer or related cancer. Any number of animal models are available. For example, surgical orthotopic implantation of histologically intact fragments of human prostate cancer may be transplanted to immunodeficient animals such as rodents. See, for example, Hoffman (1999); Segawa et al. (2000).

There are also a range of in vitro models such as those described in the Examples herein or by Anidjar et al. (2001).

The present invention is further described by the following non-limiting Examples.

EXAMPLE 1

Materials and Methods

Cells were cultured in RPMI1640 medium-10% w/v FCS in 5% v/v $CO_2$ and 5% v/v oxygen. The latter reproduces physiological conditions and is considered useful in assessing the molecular responses of normal and tumor cells to drugs. Inhibition of cell growth was determined 5-7 days after drug treatment by assay of cell numbers with sulforhodamine B (SRB) in microtitre plates.

General cell signalling activity of the E. peplus compounds is quantitated by a sensitive assay which the present inventors have developed, in which cells are simultaneously treated with the drug and infected with a non-relicating adenovirus containing the CMV promoter, which drives expression of β-galactosidase (in place of E1a). Approximately 24 hours later, the β-galactosidase activity is measured in an ELISA reader. The sensitivity of this assay (<1 ng/ml TPA) is sufficient to measure bioactivity in blood and organs and serves as the basis for comparison of structures and for translating doses determined in the mouse to humans.

Primary, short-term cultures of adherent tumor cells are established from aspirates for drug treatments.

DNA flow cytometry (FACSCAN) is used for determining effects on the cell cycle.

Microarrays of 4000 human cDNA sequences spotted on microscope slides are hybridized with fluorescent-labelled cDNA from reverse-transcribed cellular mRNA and quantitated as described by Bowtell (1999).

EXAMPLE 2

Pre-Treatment of Human Tumor Cells in Culture with Diterpene Esters Potentiates Selective Killing by Untreated Leukocytes The question of whether drug treatment of the target tumor cells causes them to become susceptible to effector cells of the immune system was addressed as follows.

Leukocytes obtained by lysis of human peripheral blood were added to 5000 MM96L human melanoma cells or 7000 neonatal foreskin fibroblasts per microtitre well at effector: target ratios of 1000, 100 and 10:1. The target cells had been treated with 60 ng/mL PEP008 for 20 hr beforehand, and washed and the medium replaced before the leukocytes were added. After 48 hr incubation with the leukocytes the cultures were washed and labelled with [3H]-thymidine for 2 hr. At 100:1 ratio of effector:target cells, the melanoma cells showed 12% survival with PEP00S whereas the normal fibroblasts had 100% survival. Untreated leukocytes had no effect on cell survival.

This result showed that the drugs also act by making tumor cells specifically sensitive to lysis by the immune system.

EXAMPLE 3

Effect of E. peplus Sap on Prostate Cancer Cells

The ability of E. peplus sap to kill prostate cancer cells selectively was assessed by comparing the effect of the sap on prostate cancer cell lines and on normal fibroblasts.

Three prostate cancer cell lines were used; PC-3 and DU145 are hormone resistant prostate cancer cell lines and LNcap is a hormone-sensitive prostate cancer cell line.

The prostate cancer cell lines or normal fibroblasts were suspended to a concentration of $5 \times 10^3$ cells/well in RPMI1640 tissue culture medium containing 10% w/v FCS, volume 0.1 ml in microtitre plates.

The cells were incubated for 6 hr at 37° C., followed by the addition of E. peplus crude sap (approximately 110 mg dry solids per ml) to the final dilutions, as shown in FIG. 1. After 5 days, cells were scored visually for survival morphology changes and survival was also assessed by $^3$H-thymidine incorporation into cell mass. The results are expressed as percentages of cell survival relative to the control (cells without drug treatment).

It can be seen that there was a concentration-dependent inhibition of all three prostate cancer cell lines, whereas normal fibroblasts remained unaffected or increased in number of concentrations of sap below 100 µg/ml.

EXAMPLE 4

The In Vitro Activity of the Pure Compounds

E. peplus compounds already known to be active on other tumor types are tested for growth inhibition of the three prostatic cancer cell lines used in Example 1 and against primary cultures of tumor cells obtained by aspiration of bone marrow metastases from patients. Three patient samples are considered sufficient to confirm potency and selectivity in humans; approximately 20 suitable patients, who have accessible bone metastases in the spine, but are well enough to undergo the procedure, are available in Brisbane each year.

The E. peplus compounds are compared to TPA and Taxol as regards potency and selectivity against tumor cells.

The two best candidate compounds, which are shown to be potent and selective compared with activity against normal fibroblasts and bladder endothelial cells are then evaluated in xenografts of tumor cells in nude mice. This model is widely used in the art (see, for example, Agus et al., 1999; El Etreby et al., 2000; Navone et al., 1998) and is sufficient to evaluate drugs for treatment of metastatic disease. The diterpenes are lipophilic and are expected to be capable of reaching the bone marrow. Moreover, less polar derivations of the ingenane, pepluane and jatrophane structures are readily prepared, for example, by acylation of the C8 hydroxyl of the jatrophanes.

EXAMPLE 5

Optimizing the Use of the E. peplus Compound

It is expected that, as found by Han et al. (1998) for TPA and by others for Taxol, the drug dose can be increased in the presence of an anti-inflammatory agent such as prednisolone.

The optimum level of prednisolone is determined in the mouse model and then the dose of diterpene increased, in order to obtain maximum non-toxic daily dosing for at least three days.

On the basis of the anticipated cell cycle arrest by E. peplum diterpenes and from results with TPA, it is expected that a range of currently available drugs such as hydroxyurea, topoisomerase inhibitors and other PKC inhibitors will synergize the action of the E. peplus diterpenes if administered at a suitable time. This is assessed in two ways. The candidate drugs are given to cultured prostatic cancer cells (cell lines and fresh tumor cells) at different temporal combinations with E. peplus diterpenes, to ascertain synergism. Second, cDNA microarray profiling is carried out, preferably with fresh cultures and cDNA amplification used to determine the changes in gene expression induced by these drugs in prostate cancer cells. Changes that are exploited pharmacologically are followed up in vitro and then in vivo.

In a third approach, the most active diterpenes are chemically linked to methylene diphosphonate (MDP), a bone-seeking compound commonly used as an imaging agent (Norris et al., 1999) and the activity of the conjugate tested against prostate cancer cells. The diterpenes are aliphatic esters which should be capable of an exchange reaction with a suitable derivative of MDP and would then be released by esterase activity in the bone marrow. The diterpenes have been found to be stable in human plasma and are not toxic to lymphoid cells. Combining physical and biological selectivity in this way may be highly advantageous.

EXAMPLE 6

Clinical Trial

It is estimated that 200-300 new cases of advanced prostate cancer present each year in Brisbane and the power of evaluation by the prostate specific antigen (PSA) test (Schroder et al., 2000) is such that only 20 patients will be required in the first instance if a 50% drop in PSA is taken as an indicator of response. Sterile diterpene and anti-inflammatory are administered iv., essentially as described by Han et al. (1998) for TPA except that the first dose is ⅓ of the bioactivity of the amount of TPA used by Han et al. (1998) (based on the range of in vitro and in vivo data available). This dose is subsequently escalated. Vital signs are monitored closely during the first 48 hr. Blood profiles, including PSA, are measured weekly for four weeks, at which time a decision is made whether to repeat the treatment. A similar protocol is used for experiments involving intralesional injections and for the use of slow release formulations, beads or capsules.

The level of active diterpene in the blood is detected by bioassay on a tumor cell line as assessed by induction of β-galactosidase due to transcriptional activation of the CMV promoter; the sensitivity of the assay is <1 ng/ml, which can be further enhanced by solvent extraction, concentration and HPTLC, if necessary. The changes in PSA (natural log PSA; Schroder et al., 2000; Vollmer et al., 1999) and other clinical indicators are correlated to determine the outcome of the trial. A reduction in PSA of >50% over three months is sought; however, pain relief, stabilization of disease and bone scans are also considered.

EXAMPLE 7

Topical Treatment of DU145 Prostate Tumor in Nude$^{(nu-/nu-)}$ Mice with PEP003

To assess whether the *E. peplus* compounds reduce tumors in mice, a DU145 prostate tumor was implanted into nude$^{(nu-nu-)}$ mice and treated with PEP003 (see Table 1). Ten mice were divided up into two groups of four mice and six mice, a control group and a treatment group, respectively. In both groups, each mouse was injected (s.c.), with 1×10$^6$ (50 µl) DU145 prostate tumor cells into each of two sites. After 20 days, the tumor was visible (4 mm$^3$). In the control group, all tumor sites were treated by a single topical application of 2 µl of 100% v/v acetone. In the treatment group, all tumor sites were treated by a single topical application of 2 µl of PEP003 in 100% v/v acetone, containing approximately 50 µg of PEP003. The mice were observed for nine weeks and the tumor size measured. Control mice were sacrificed before tumor burden became excessive.

Figure 2:
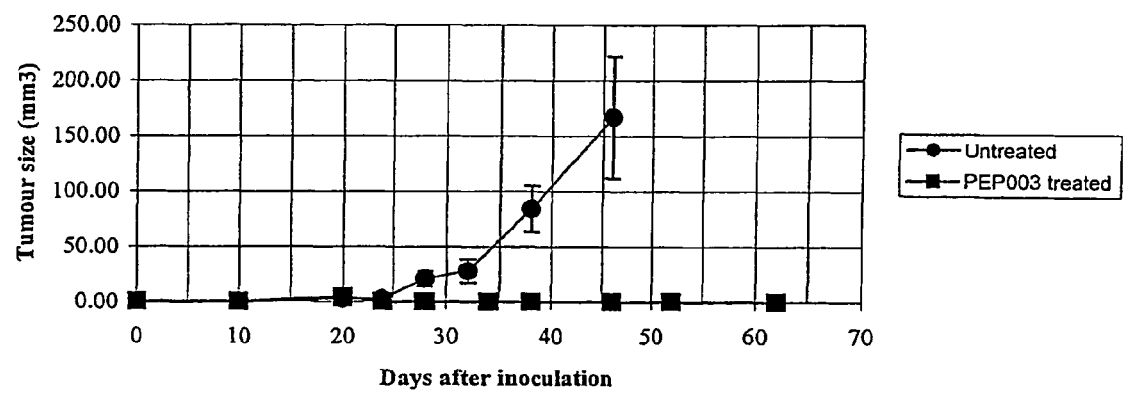
FIG. 2 is a graphical representation of the effects of topical administration of PEP003 from *E. peplus* on DU145 tumors in nude mice.

The results (FIG. 2) show a rapid increase of DU145 prostate tumor in the control group, to an average tumor size of 167 mm$^3$, 46 days post inoculation. The results also show that treatment of DU145 prostate tumor by topical application of PEP003 cured the tumor, without re-growth after 62 days.

The data clearly show that topical application of PEP003 onto subcutaneous DU145 prostate tumors in nude$^{(nu-/nu-)}$ mice causes tumor cure.

EXAMPLE 8

Topical Treatment of PC-3 Prostate Tumor in Nude $^{(nu-/nu-)}$ Mice with PEP003

To assess whether the *E. peplus* compounds reduce tumors in mice, PC-3 prostate tumor was implanted into nude$^{(nu-/nu-)}$ mice and treated with PEP003 (see Table 1). Thirteen mice were divided up into two groups of five mice and eight mice, a control group and a treatment group, respectively. In both groups, each mouse was injected (s.c.), with 1×10$^6$ (50 µl) PC-3 prostate tumor cells into each of two sites. After three days, the tumor was visible (4 mm$^3$). In the control group, all tumor sites were treated by a single topical application of 2 µl of 100% v/v acetone. In the treatment group, all tumor sites were treated by a single topical application of 2 µl of PEP003 in 100% v/v acetone, containing approximately 50 µg of PEP003. The mice were observed for five weeks and the tumor size measured. Control mice were sacrificed before tumor burden became excessive.

Figure 3:
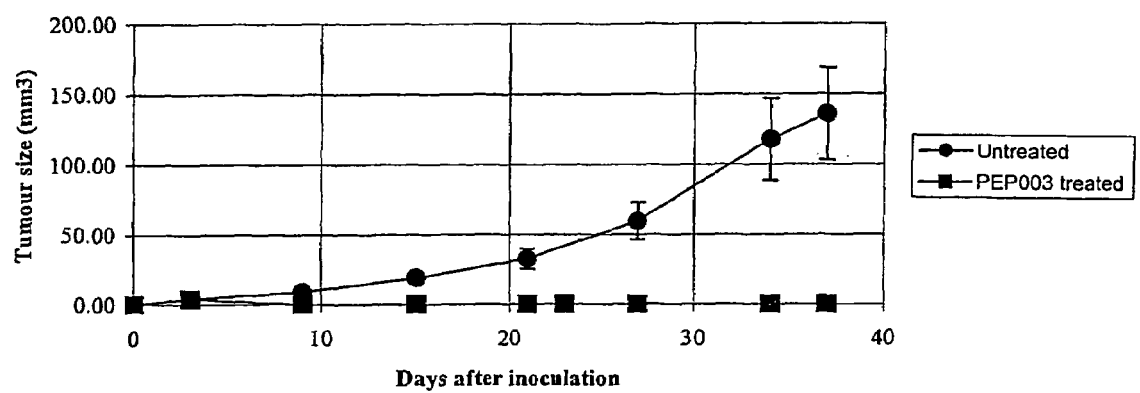
FIG. 3 is a graphical representation of the effects of topical administration of PEP003 from *E. peplus* on PC-3 tumors in nude mice.

The results (FIG. 3) show a rapid increase of PC-3 prostate tumor in the control group, to an average tumor size of 136 mm$^3$, 37 days post inoculation. The results also show that treatment of PC-3 prostate tumors by topical application of PEP003 cured the tumor, without re-growth after 37 days.

The data clearly show that topical application of PEP003 onto subcutaneous PC-3 prostate tumors in nude$^{(nu-/nu-)}$ mice causes tumor cure.

EXAMPLE 9

Intralesional Treatment of PC-3 Prostate Tumor in Nude(nu-/nu-) Mice with PEP003

To assess whether the *E. peplus* compounds reduce tumors in mice, PC-3 prostate tumor was implanted into nude$^{(nu-nu-)}$ mice and treated with PEP003 (see Table 1). Ten mice were divided up into two groups of six mice and four mice, a control group and a treatment group, respectively. In both groups, each mouse was injected (s.c.), with 1×10$^6$ (50 µl) PC-3 prostate tumor cells into each of two sites. After six days, the tumor was visible (1 mm$^3$). In the control group, all tumor sites were treated by a single intralesional injection of 10% v/v acetone in saline. In the treatment group, all tumor sites were treated by a single intralesional injection of 10% v/v acetone in saline (50 µl), containing approximately 6.25 µg of PEP003. The mice were observed for 19 weeks and the tumor size measured. Control mice were sacrificed before tumor burden became excessive.

Figure 4:
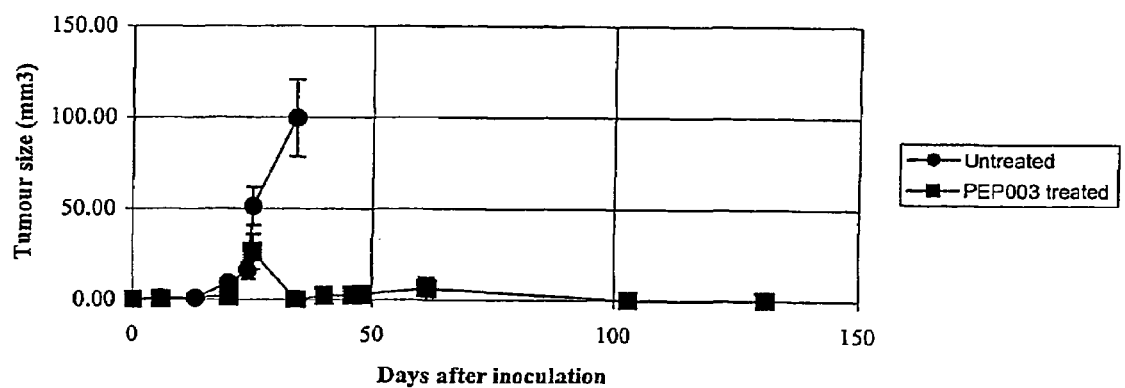
FIG. 4 is a graphical representation of the effects of intralesional treatment by PEP003 on PC-3 tumors in nude mice.

The results (FIG. 4) show a rapid increase of PC-3 prostate tumor in the control group, to an average tumor size of 100 mm$^3$, 34 days post inoculation. The results also show that treatment of PC-3 prostate tumors by intralesional injection of PEP003 cured the tumor, without re-growth after 131 days.

The data clearly show that intralesional injection of the PEP003 onto subcutaneous PC-3 prostate tumors in nude$^{(nu-nu-)}$ mice causes tumor cure.

EXAMPLE 10

Intralesional Treatment of DU145 Prostate Tumor in Nude(nu-/nu-) Mice with PEP003

To assess whether the *E. peplus* compounds reduce tumors in mice, DU145 prostate tumor was implanted into nude$^{(nu-nu-)}$ mice and treated with PEP003 (see Table 1). Six mice were divided up into two groups of four mice and two mice, a control group and a treatment group, respectively. In both groups, each mouse was injected (s.c.), with 1×10$^6$ (50 µl) DU145 prostate tumor cells into each of two sites. After 20 days, the tumor was visible (2 mm$^3$). In the control group, all tumor sites were treated by a single intralesional injection of 10% v/v acetone in saline. In the treatment group, all tumor sites were treated by a single intralesional injection of 10% v/v acetone in saline (50 µl), containing approximately 2.5 µg of PEP003. The mice were observed for nine weeks and the tumor size measured. Control mice were sacrificed before tumor burden became excessive.

Figure 5:
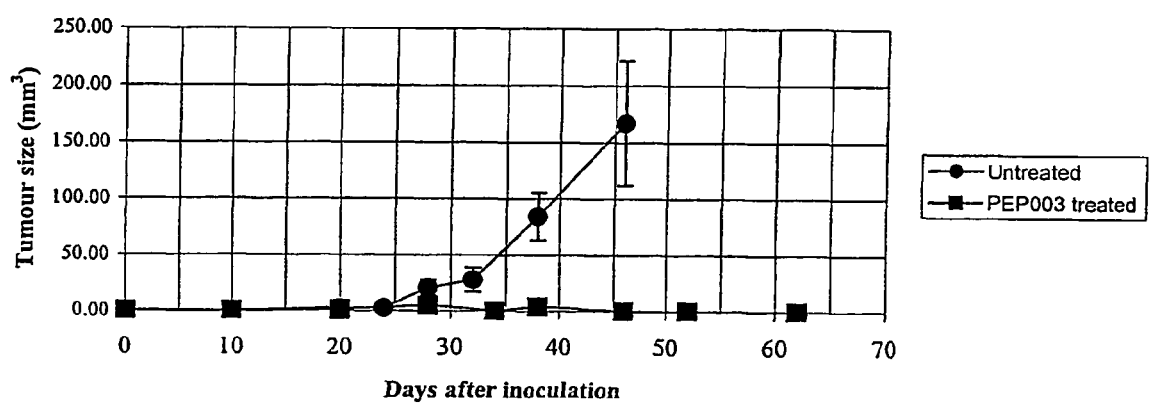
FIG. 5 is a graphical representation of the effects of intralesional treatment by PEP003 on DU145 tumors in nude mice.
Figure 6A:
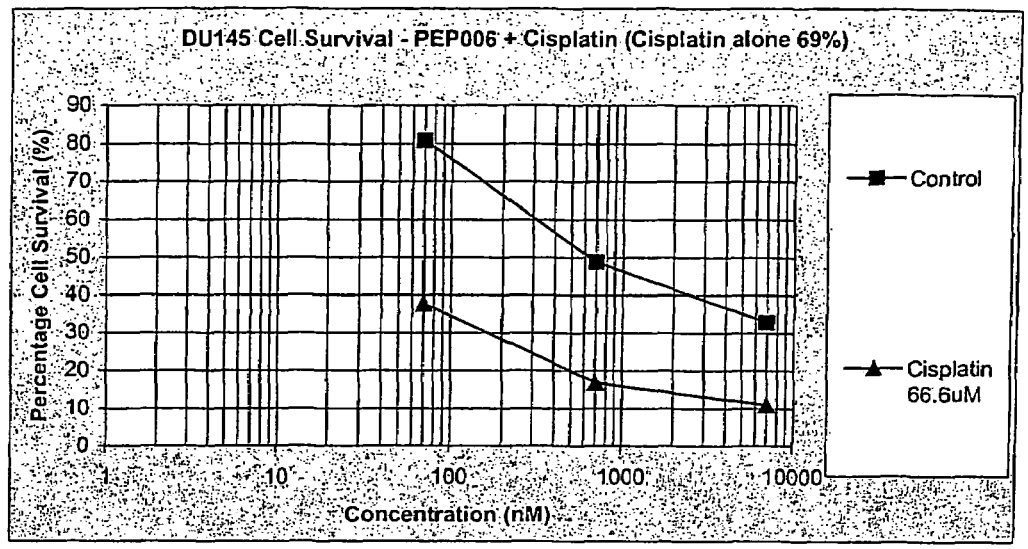
FIGS. 6A to 6E are graphical representations showing the synergistic behaviour of angeloyl-substituted ingenanes in combination with chemotherapeutic agents on killing DU145 cells.
Figure 6B:
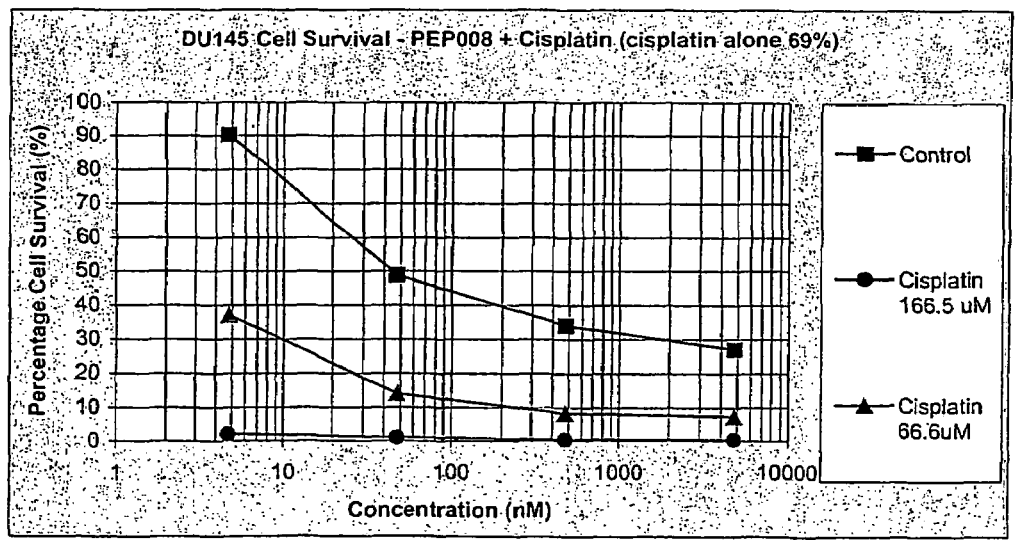
Figure 6C:
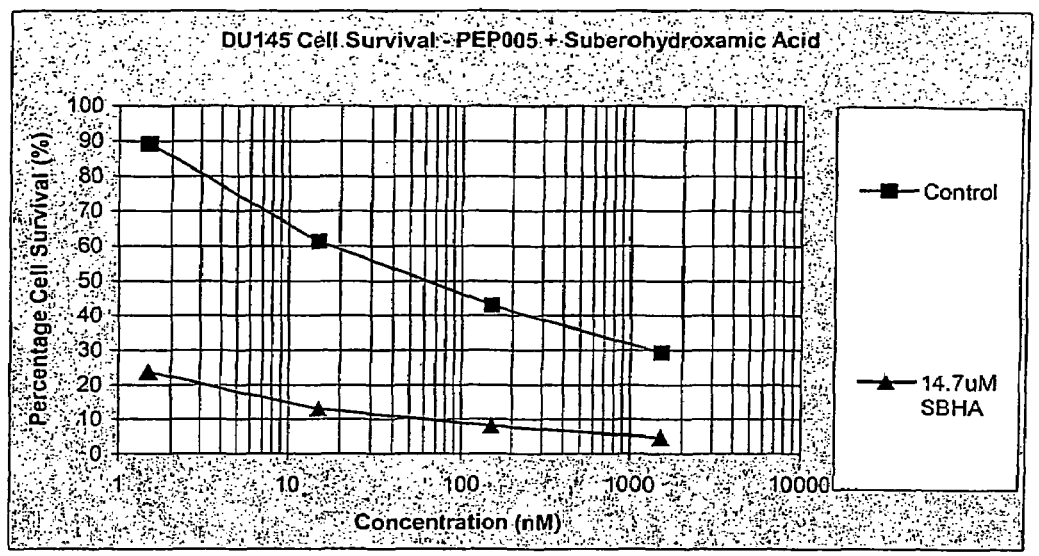
Figure 6D:
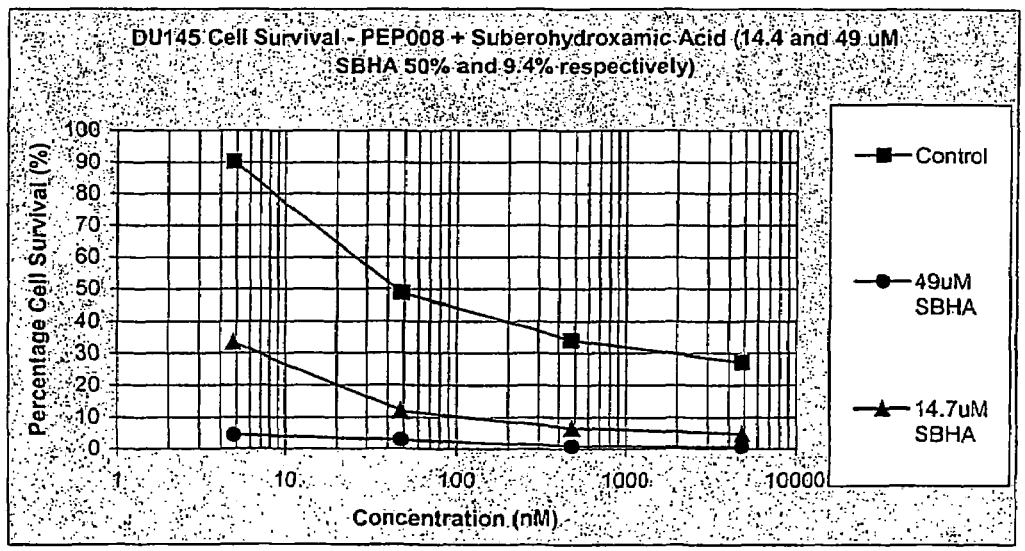
Figure 6E:
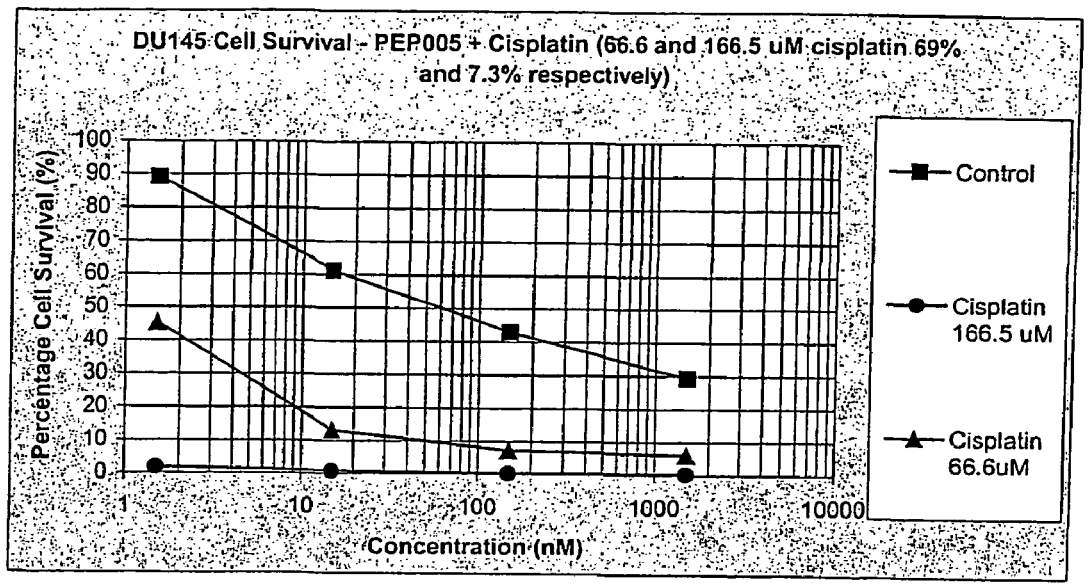

The results (FIG. 5) show a rapid increase of DU145 prostate tumor in the control group, to an average tumor size of 167 mm$^3$, 46 days post inoculation. The results also show that treatment of DU145 prostate tumors by intralesional injection of PEP003 cured the tumor, without re-growth after 62 days.

The data clearly show that intralesional injection of PEP003 onto subcutaneous DU145 prostate tumors in nude$^{(nu-nu-)}$ mice causes tumor cure.

EXAMPLE 11

Synergisitic Combination of PEP005, PEP006 or PEP008 with Cisplatin or Suberic Dihydroxamic Amino Acid on DU145 Prostate Cancer Cell Cytotoxicity DU145 prostate cancer cells were treated with a drug combination comprising a purified preparation of an angeloyl-substitued ingenane selected from PEP005, PEP006 or PEP008 and a chemotherapeutic agent selected from cisplatin or suberic dihydroxamic amino acid (SBHA) to assess whether such combination displays synergistic effects on prostate cancer cytotoxicity.

The prostate cancer cells were treated with (A) PEP006 and cisplatin, (B) PEP008 and cisplatin, (C) PEP005 and SBHA, (D) PEP008 and SBHA and (E) PEP005 and cisplatin for 24 hr after which the medium was changed and the cells permitted to grow in the presence of $^3$H-thymidine for five days. The percentage cell survival was determined by measuring the incorporation of $^3$H-thymidine in the cells.

The results presented in FIGS. 6A to 6E indicate that combinations of cisplatin or SBHA together with PEP005, PEP006 or PEP008 produce greater cytotoxicity compared to the additive cytotoxicity of the compounds when administered alone and are, therefore, synergistic combinations.

EXAMPLE 12

Methods for Obtaining a Low-Chlorophyll, Hydrophobic Fraction from *E. peplus* and Other Plant Species Standard methods for the isolation of hydrophobic compounds from plants involve alcoholic extraction of the whole plant. This produces an extract containing chlorophyll and other hydrophobic substances from the leaves that interfere with subsequent purification of compounds by solvent extractions and chromatography. This is a particular problem in isolating highly bioactive diterpenes from members of the Euphorbiaceae family, due to co-migration with chlorophyll on silica gel chromatography. Two methods, both of which can be scaled up for economical, commercial production, have been developed to overcome this problem, as described in the present Example and in Example 14.

Fresh *E. peplus* plants (17 kg) were chopped and soaked in 150 litres of water at 4° C. for 20 hr. The water was pumped through 50 and 100 mesh sieves, filtered through 5 and 2 micron filters and then recirculated through a 100 mm diameter column of Amberlite XAD-16 (1.5 kg, conditioned successively with ethyl acetate, methanol and water) at 4° C. (approximately 1.2 L/min) for 72 hr. Adsorption of bioactivity to the resin was found to be virtually complete within 20 hr.

The resin was then washed successively with water and 50% v/v methanol, then eluted with 1 L of methanol, followed by 2×1 L acetone. The eluates were evaporated and combined to give approximately 7 g of a thick oil. This was shown by BPTLC to be substantially free of chlorophyll and to contain the desired ingenane esters which were then purified as described below.

The ability to extract diterpene esters from chopped plants in water was surprising given their relative hydrophobicity and water insolubility. A variety of manual (cutting with scissors) and mechanical (rotary cutters, motor-driven mulcher) plant maceration methods were successful, as was extraction at room temperature. Adsorption to the XAD-16 could be achieved by stirring the resin with the filtered or unfiltered water extract and then pouring off the latter. Filtration could also be carried out with minimal loss of bioactivity using diatomaceous earth, or membrane filters (220-650 microns). XAD-7 and XAD-4 were as effective as XAD-16.

The hydrophobic adsorbent polyamide (I CN Biomedical Research Products) was also used to trap the diterpenes from water; it had the advantage of allowing the diterpene esters to be selectively eluted with 50-80% v/v methanol, thus separating them from inactive, hydrophobic compounds, which remained on the column.

EXAMPLE 13

Method for Separation of Ingenane Esters from Other Diterpenes

The following method is based upon the surprising discovery that the stems of *E. peplus* contain approximately 90% of the bioactive diterpenes and significantly less chlorophyll compared with the leaves.

The plants are dried in air, shaken to remove the leaves and the stems compressed and covered with an equal weight of methanol for 24 hr. The solvent is then poured off, evaporated to dryness under reduced pressure and the residue dissolved in methanol for chromatography on Sephadex LH-20 as described below. This method is also suitable for isolation of low-chlorophyll fractions from other plant species.

A solution of crude methanol extract from *E. peplus* in 4 mL 90% v/v ethanol was loaded onto a 25 mm×1000 mm column and eluted with 90% v/v methanol. Fractions (4 mL) were analyzed by HPTLC (silica gel, developed with 4:1 toluene: acetone and heated with phosphoric acid at 110° C. for 15 min). Typically, fractions 54-63 contained jatrophane and pepluane esters and fractions 64-77 the ingenane esters, thus achieving satisfactory separation. Bioactivity, as judged by induction of bipolar morphology in the human melanoma cell line MM96L, was retained as, for example, disclosed in International Patent Application No. PCT/AU98/00656.

This separation was surprising because the polarity of the ingenane esters as judged by HPTLC on silica completely overlapped the range shown by the jatrophane and pepluane esters.

EXAMPLE 14

Process for the Purification of Diterpene Esters from *E. peplus*

Crude extracts obtained by the methods according to Examples 17 or 18 above, or by ether extraction of latex, were fractionated by Sephadex HL-20 chromatography (as above). Appropriate fractions from the latter were combined, the methanol evaporated under reduced pressure and the remaining water removed by freeze-drying or by ether extraction. This sample (200 µL of 100 mg/mL in methanol per injection) was fractionated by HPLC on a Phenomenex Luna 250×10 mm C18 column with a Phenomenex guard column in 70-100% v/v methanol at 2 mL/min, with detection at 230 nm. Jatrophane and pepluane esters appeared at 25-42 min, PEP005 at 42-44 min, PEP008 at 46-50 min, and PEP006 at 50-54 min. Similar types of separation have been obtained by HPLC on C3 and C8 columns.

Fractions pooled from repeated runs were evaporated to dryness (rotary evaporater or freeze dryer) and stored in acetone at −20° C. under argon or nitrogen.

Speculative procedures for synthesis of bisphosphonate substituted ingenanes.

EXAMPLE 15

Synthesis of 20-chloro-20-deoxyingenol 3,5-dibenzoate from ingenol—Scheme 1

Ingenol can be converted to 20-chloro-20-deoxyingenol 3,5-dibenzoate by the procedure reported in Appendino et al. (1999). Thus, ingenol can be converted to ingenol 20-trityl ether by treatment with trityl chloride and 4-(N,N-dimethylamino)pyridine in dry pyridine. Ingenol-20-trityl ether can be converted to ingenol 3,5-benzoate by treatment with benzoic acid, 1-(3-dimethylaminopropyl)-3-ethylcarbodiimide hydrochloride and dimethyl-aminopyridine in dichloromethane followed by reaction with methanolic perchloric acid. Ingenol 3,5-dibenzoate can be converted to 20-chloro-20-deoxyingenol 3,5-dibenzoate by reaction with hexachloroacetone and triphenylphosphine in dry dichloromethane.

EXAMPLE 16

Synthesis of 20-chloro-20-deoxyingenol 3,5-dibenzoate from ingenol 3-angelate

Ingenol 3-angelate extracted from *Euphorbia* species could be converted to 20-chloro-20-deoxyingenol 3-angelate 5-benzoate by the method of Example 15.

EXAMPLE 17

Synthesis of 20-chloro-20-deoxyingenol 3,5-dibenzoate from ingenol—Scheme 2

Ingenol is reacted with p-toluenesulphonic acid hydrate and acetone to give ingenol-5,20-acetonide according to the procedure of Opferkuch et al. (1981). Ingenol-5,20-acetonide is converted to the ingenol 3-acylate by treatment with the appropriate acyl chloride and 4-(N,N-dimethylamino)pyridine or pyridine in toluene or benzene, or treatment with the appropriate acid, an alkylpyridinium salt and tributylamine in toluene then treatment with methanolic perchloric acid according to the procedure of Sorg et al. (1982). The ingenol 3-acylate could be converted to the 20-chloro-20-deoxyingenol 3-acylate 5-benzoate by the method of Example 15.

EXAMPLE 18

Synthesis of 20-chloro-20-deoxyingenol 3,5-dibenzoate from ingenol—Scheme 3

Ingenol can be converted to ingenol-3,4-acetonide by treatment with 4-toluenesulphonic acid hydrate and acetone to give ingenol-3,4:5,20-diacetonide followed by treatment with perchloric acid in methanol or zinc bromide in dichloromethane and methanol according to the method of Opferkuch et al. (1981). Ingenol-3,4-acetonide could be converted to ingenol-3,4-acetonide-20-trityl ether by treatment with trityl chloride and 4-(N,N-dimethylamino)pyridine in dry pyridine, acylated in an analogous manner to that described in Example 1 or Example 3 to give the ingenol-3,4-acetonide-20-trityl ether 5-acylate then treated with methanolic perchloric acid according to the method of Example 15 or Example 18 to give the ingenol 5-acylate. The ingenol 5-acylate could then be converted to the ingenol-3,4-acetonide 5-acylate by treatment with 4-toluenesulphonic acid hydrate and acetone according to the method of Opferkuch et al. (1981). The ingenol-3,4-acetonide 5-acylate could be converted to the 20-chloro-20-deoxy-3,4-acetonide 5-acylate by the method of Example 15.

EXAMPLE 19

Preparation of tetraalkyl phthalimido-1-hydroxyalkylbisphosphonates

Tetraalkyl phthalimido-1-hydroxyalkylbisphosphonates can be prepared by the method of El Manouni et al. (1989). These could be converted to the corresponding tetraalkyl amino-1-hydroxyalkylbisphosphonates by standard treatment with hydrazine hydrate in ethanol.

EXAMPLE 20

Synthesis of Bisphosphonic Acid Derivatives of Acylingenols 20-chloroingenol acylates from Examples 17-20 could be reacted with 1,1-bis(dialkoxyphosphoryl)-1-hydroxyalkylamines, triphenylphosphine, diethylazodi-carboxylate and tetrahydrofuran to give 20-[bis(dialkoxyphosphoryl)hydroxyalkylamino]-20-deoxy-3-O-acylingenols and 20-[bis(dialkoxyphosphoryl)hydroxyalkylamino]-20-deoxy-5-O-acylingenols according to the procedure of Appendino et al. (1999). 20-[Bis(dialkoxyphosphoryl)hydroxyalkylamino]-20-deoxy-3-O-acylingenols and 20-[bis(dialk-oxyphosphoryl)hydroxyalkylamino]-20-deoxy-5-O-acylingenols could be converted to the corresponding 20-[bis(dihydroxyphosphoryl)hydroxyalkylamino]-20-deoxy-3-O-acylingenols and 20-[bis(dihydroxyphosphoryl)hydroxyalkylamino]-20-deoxy-5-O-acylingenols by treatment with bromotrimethylsilane or iodotrimethylsilane and solvolysis with alcohol or water according to Lecouvey et al. (2000) and references therein. The bisphosphonic acids could be converted to the appropriate salts by careful titration with an inorganic base, for example, sodium hydroxide.

EXAMPLE 21

Synthesis of ingenol-3-acylate-20-trityl ethers from ingenol-3-acylates

Ingenol-3-acylates could be converted to the corresponding ingenol-3-acylate-20-trityl ethers by the method of Example 17. Ingenol-3-acylate-20-trityl ethers could be converted to 5-(chloromethylcarbonyloxy)ingenol-3-acylate-20-trityl ethers or 5-(bromomethyl-carbonyloxy)ingenol-3-acylate-20-trityl ethers by reaction with chloroacetyl chloride or bromoacetyl chloride and 4-(N,N-dimethylamino)pyridine in pyridine and dry ether according to the procedure of Nangia et al. (1996). 5-(Chloromethylcarbonyloxy)ingenol-3-acylate-20-trityl ether or 5-(bromomethylcarbonyloxy)ingenol-3-acylate-20-trityl ethers could be converted to 5-[bis(dialkoxyphosphoryl)hydroxyalkylaminomethylcarbonyloxy]-ingenol-3-acylate-20-trityl ethers by the method of Example 6 and then converted to 5-[bis(dialkoxyphosphoryl)hydroxyalkylaminomethylcarbonyloxy]ingenol-3-acylates by the method of Example 15. These could then be converted to [bis(dihydroxy-phosphoryl)hydroxyalkylaminomethylcarbonyloxy]ingenol-3-acylates or salts thereof by the method of Example 20.

EXAMPLE 22

Synthesis of -[bis(dihydroxyphosphoryl)hydroxyalkylaminomethylcarbonyloxy]ingenols (9S)-9-Deoxo-9-hydroxyingenol-3,4:5,20-diacetonide can be prepared from ingenol-3,4:5,20-diacetonide by reduction with lithium aluminium hydride in tetrahydrofuran and (9R)-9-deoxo-9-hydroxyingenol-3,4:5,20-diacetonide can be prepared from ingenol-3,4:5,20-diacetonide by reduction with sodium in 2-propanol and ether according to the procedure of Bagavathi et al. (1991). (9S)-or (9R)-9-Deoxo-9-hydroxyingenol-3,4:5,20-diacetonide could be converted to (9S)-or (9R)-9-deoxo-9-(chloromethyl-carbonyloxy)ingenol-3,4:5,20-diacetonide or (9S)-or (9R)-9-deoxo-9-(bromomethyl-carbonyloxy)ingenol-3,4:5,20-diacetonide by reaction with chloroacetylchloride or bromoacetylchloride and 4-(N,N-dimethylamino)pyridine in pyridine and dry ether according to the procedure of Nangia et al. (1996). (9S)-or (9R)-9-Deoxo-9-(chloromethylcarbonyloxy)ingenol-3,4:5,20-diacetonide or (9S)-or (9R)-9-deoxo-9-(bromomethylcarbonyloxy)ingenol-3,4:5, 20-diacetonide could be converted to the corresponding (9S)-or (9R)-9-deoxo-9-[bis(dialkoxyphosphoryl)hydroxyalkylamino-methylcarbonyloxy]ingenol-3,4:5,20-diacetonide by the method of Example 6. (9S)-or (9R)-9-Deoxo-9-[bis(dialkoxyphosphoryl)hydroxyalkylaminomethylcarbonyloxy]ingenol-3,4:5,20-diacetonide could be treated with methanolic perchloric acid followed by 4-toluenesulphonic acid hydrate to give (9S)-or (9R)-9-deoxo-9-[bis( dialkoxyphosphoryl)-hydroxyalkylaminomethylcarbonyloxy]ingenol-5,20-acetonide according to the method of Example 17. This in turn could be converted to (9S)-or (9R)-3-acyl-9-deoxo-9-[bis(dialkoxyphosphoryl)hydroxyalkylaminomethylcarbonyloxy]ingenol-5,20-acetonides then (9S)-or (9R)-3-acyl-9-deoxo-9-[bis(dialkoxyphosphoryl)hydroxyalkylaminomethylcarbonyloxy]ingenols by the method of Example 19. These could then be converted into (9S)-or (9R)-3-acyl-9-deoxo-9-[bis(dihydroxyphosphoryl) hydroxyalkylaminomethylcarbonyloxy]ingenols and salts thereof by the method of Example 20.

EXAMPLE 23

Acylated Tetraalkyl Bisphosphonate Deriviatives of Ingenol

Tetraalkyl bisphosphonate derivatives of ingenol can be further acylated on any free hydroxyl groups selected from the 3-OH, 5-OH and 20-OH by treatment with an appropriate acyl chloride and 4-(N,N-dimethylaminopyridine) or pyridine in toluene or benzene according to the procedure of Sorg et al. (1982), then converted to the bisphosphonic acid derivatives of ingenol or salts thereof by the method of Example 20.

EXAMPLE 24

Preparation of deoxyingenol 3,5-diacylates from 20-deoxy-17-hydroxy-ingenol

20-Deoxy-17-hydroxy-ingenol obtained by hydrolysis of esters from *Euphorbia* species could be converted to 20-deoxy-17-hydroxy-ingenol 3,5-diacylate 17-trityl ethers then to 20-deoxy-17-hydroxy-ingenol 3,5-diacylates and 17-chloro-20-deoxyingenol 3,5-diacylates by the method of Example 15. These could then be converted to 17-[bis (dihydroxyphosphoryl)hydroxyalkylamino]-20-deoxyingenol 3,5-diacylates and salts thereof by the method of Example 20.

EXAMPLE 25

Preparation of bisphosphonate derivatives of acylingenols

17-Hydroxyingenol obtained by hydrolysis of esters from *Euphorbia* species could be converted to 17-hydroxyingenol-3,4:5,20-diacetonide by the method of Example 18 and thence to 17-chloroingenol-3,4:5,20-diacetonide by the method of Example 15. This could then be converted to 17-chloroingenol by treatment with methanolic perchloric acid and converted to 17-chloroingenol-5,20-acetonide then to 3-acyl-17-chloroingenols by the method of Example 17. 3-Acyl-17-chloroingenols could be converted to 17-[bis (dihydroxyphosphoryl)hydroxyalkylamino]-20-deoxy-3-O-acylingenols and salts thereof by the method of Example 20. Further acylation of these could be achieved by the method of Example 23.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Agus et al., *Cancer Res.* 59; 4761-4764, 1999.
Anidjar et al., *Prostate* 46: 2-10, 2001.
Antalis et al., *J. Exp. Med.* 187: 1799-1811, 1998.
Appendino et al., *Eur. J. Org. Chem.* 3413-3420, 1999.
Bagavathi et al., *Z. Naturforsch* 46b: 1425-1433, 1991.
Botwell, *Nature Genet* 21: 25-32, 1999.
Bushnell et al., *Nucl. Med. Commun.* 20: 875-881, 1999.
Christenson et al., *Endothelium* 7: 75-82, 1999.
El Etreby et al., *Prostate* 42: 99-106, 2000.
Elliott et al., *Vaccine* 17: 2009-2019, 1999.
El Manouni et al., *Phosphorus Sulfur and Silicon* 42: 73-83, 1989.
Evans & Osman, *Nature* 250: 348, 1974.
Fatope et al., *J. Med. Chem.* 39: 1005-1008, 1996.
Gabizon, *Cancer Invest.* 19): 424-436, 2001.
Gonzalez et al., *Melanoma Res.* 9: 599-606, 1999.
Greaves and Wall, *Lancet* 348): 938-940, 1996.
Gundidza and Kufa, *Centr. Afr. J. Med.* 38: 444-447, 1992.
Han et al., *Proc. Natl. Acad. Sci. USA* 95: 5357-5361, 1998.
Hecker "Cocarcinogens from Euphorbiaceae and Thymeleaceae" in "*Symposium on Pharmacognosy and Phytochemistry*", 147-165, (Wagner et al., eds., Springer Verlag, 1970).
Hoffman, *Invest. New Drugs* 17: 343-359, 1999.
Hohmann et al., *J. Nat. Products* 6: 107-109, 1999.
Horsmanheimo et al., *J. Allergy Clin. Immunol.* 98: 408-411, 1996.
Imai et al., *Anticancer Res.* 14: 933-936, 1994.
Jain et al., *Drug Dev. Ind. Pharm.* 24: 703-727, 1998.
Kanellakopoulou et al., *Drugs* 59 1223-1232, 2000.
Kunisawa et al., *Gan To Kagaku Ryoho* 28): 577-583, 2001.
La Linn et al., *J. Gen. Virol.* 77: 407-412, 1996.
Lecouvey and Leroux, *Heteroatom Chemistry* 11: 556-561, 2000.
Marks et al., *Int. J Cancer* 53(4): 585-590, 1993.
Matsushita et al., *Int. J. Hematol.* 72(1): 20-7, 2000.
Miller et al., *J. Am. Acad. Dermatol.* 30(5): 774-778, 1974.
Mollinedo, *Immunol Today* 20(12): 535-7, 1999.
Muggia, *Curr. Oncol. Rep.* 3: 156-162, 2001.
Murali-Krishna et al., *Immunity* 8: 177-187, 1998.
Nangia et al., *J. Chem. Res. Miniprint* 7: 1716-1730, 1996.
Navone et al., *Cancer Metastasis Rev.* 17: 361-371, 1999.
Nishioka et al., *Adv. Drug Deliv. Rev.* 47): 55-64, 2001.
Norris et al., *Clin. Nucl. Med.* 24(11): 905-907, 1999.
Oksuz et al., *Phytochemistry* 42: 473-478, 1996.
Opferkuch et al., *Z. Naturforsch* 36b: 878-887, 1981.

Post et al., *Int. J. Epidemiol.* 28: 403-408, 1999.
Schroder et al., *Prostate* 42: 107-115, 2000.
Segawa et al, *Prostate* 45: 335-340, 2000.
Sorg and Hecker, *Z. Naturforsch* 37b: 748-756, 1982.
Starvic and Stolz, *Food Cosmet. Toxicol.* 14: 141, 1976.
Steinkamp et al., *Science* 215: 64-66, 1982.
Thomasin et al., *J. Pharm. Sci.* 87: 259-268, 1998.
Tobiume et al., *J. Gen. Virol.* 79: 1363-1371, 1998.
Vollmer and Montana, *Clin. Cancer Res* 5(9): 2476-2484, 1999.

The invention claimed is:

1. A method to facilitate amelioration of the effects of symptoms or reduce the adverse effects of a carcinoma of the bladder or potentiate the immune system components therein to ameliorate the symptoms caused or facilitated by carcinoma of the bladder in a subject, said method comprising administrating to a subject having a carcinoma of the bladder a symptom-ameliorating effective amount of a chemical agent, which chemical agent is an ingenane, said ingenane having the formula:

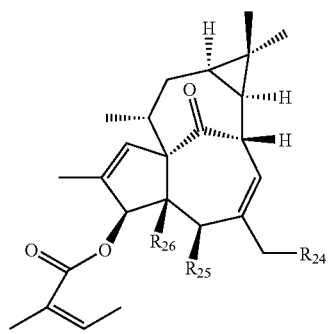

VI or pharmaceutically acceptable salts thereof,
wherein:
$R_{24}$, $R_{25}$ and $R_{26}$ are independently selected from hydrogen, $R_{27}$, $R_{28}$, F, Cl, Br, I, OH, CN, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, $B(R_{27})_2$, $(C=X)R_{29}$ or $X(C=X)R_{29}$ where X is selected from sulfur, oxygen and nitrogen;
$R_{27}$ and $R_{28}$ are each independently selected from $C_1$-$C_{20}$ alkyl (branched and/or straight chained), aryl $C_1$-$C_{20}$ alkyl, $C_3$-$C_8$ cycloalkyl, $C_6$-$C_{14}$ aryl, $C_1$-$C_{14}$ heteroaryl, $C_1$-$C_{14}$ heterocycle, $C_2$-$C_{10}$ alkenyl (branched and/or straight chained), $C_2$-$C_{10}$ alkynyl (branched and/or straight chained), $C_1$-$C_{10}$ heteroarylalkyl, $C_1$-$C_{10}$ alkoxyalkyl, $C_1$-$C_{10}$ haloalkyl, dihaloalkyl, trihaloalkyl, haloalkoxy, $C_1$-$C_{10}$ alkyl which is unsubstituted or substituted by CN, $OR_{30}$, $SR_{30}$, $NR_{30}R_{31}$, $N=(O)_2$, $NR_{30}$ $OR_{31}$, $ONR_{30}$ $R_{31}$, $SOR_{30}$, $SO_2R_{30}$, $SO_3R_{30}$, $SONR_{30}R_{31}$, $SO_2NR_{30}R_{31}$, $SO_3NR_{30}R_{31}$, $P(R_{30})_3$, $P=(O)(R_{30})_3$, $Si(R_{30})_3$, and $B(R_{30})_2$;
$R_{29}$ is selected from $R_{27}$, $R_{28}$, CN, $COR_{27}$, $CO_2R_{27}$, $OR_{27}$, $SR_{27}$, $NR_{27}R_{28}$, $N(=O)_2$, $NR_{27}OR_{28}$, $ONR_{27}R_{28}$, $SOR_{27}$, $SO_2R_{27}$, $SO_3R_{27}$, $SONR_{27}R_{28}$, $SO_2NR_{27}R_{28}$, $SO_3NR_{27}R_{28}$, $P(R_{27})_3$, $P(=O)(R_{27})_3$, $Si(R_{27})_3$, and $B(R_{27})_2$ $SO_3NR_{27}R_{28}$, $P(R_{27})_3$, $P(=O)(R_{27})_3$, $Si(R_{27})_3$, and $B(R_{27})_2$; and
each $R_{30}$ and $R_{31}$ are independently $C_1$-$C_{20}$ alkyl, $C_1$-$C_{20}$ aryl $C_1$-$C_2$ alkyl, $C_3$-$C_8$ cycloalkyl, $C_6$-$C_{14}$ aryl, $C_1$-$C_{14}$ heteroaryl, $C_1$-$C_{14}$-heterocycle, $C_2$-$C_{10}$ alkynyl, $C_2$-$C_{10}$ alkenyl, $C_1$-$C_{10}$ heteroarylalkyl, $C_1$-$C_{10}$ alkoxyalkyl, $C_1$-$C_{10}$ haloalkyl, dihaloalkyl, trihaloalkyl, or haloalkoxy.

2. The method according to claim 1 wherein $R_{24}$ is H.
3. The method according to claim 1 wherein $R_{24}$ is OAcetyl.
4. A method according to claim 1 wherein $R_{24}$ is OH.
5. A method according to claim 1 wherein $R_{25}$ and $R_{26}$ are OH.
6. The method according to claim 1 wherein $R_{25}$ is OH.
7. The method according to claim 1 wherein $R_{26}$ is OH.
8. The method according to claim 1 wherein the chemical agent is obtainable from a species of *Euphorbia*.
9. The method according to claim 8 wherein the species of *Euphorbia* is selected from *Euphorbia aaron-rossii*, *Euphorbia abbreviata*, *Euphorbia acuta*, *Euphorbia alatocaulis*, *Euphorbia albicaulis*, *Euphorbia algomarginata*, *Euphorbia aliceae*, *Euphorbia alta*, *Euphorbia anacampseros*, *Euphorbia andromedae*, *Euphorbia angusta*, *Euphorbia anthonyi*, *Euphorbia antiguensis*, *Euphorbia apocynifolia*, *Euphorbia arabica*, *Euphorbia ariensis*, *Euphorbia arizonica*, *Euphorbia arkansana*, *Euphorbia arteagae*, *Euphorbia arundelana*, *Euphorbia astroites*, *Euphorbia atrococca*, *Euphorbia baselicis*, *Euphorbia batabanensis*, *Euphorbia bergeri*, *Euphorbia bermudiana*, *Euphorbia bicolor*, *Euphorbia biformis*, *Euphorbia bifurcata*, *Euphorbia bilobata*, *Euphorbia biramensis*, *Euphorbia biuncialis*, *Euphorbia blepharostipula*, *Euphorbia blodgetti*, *Euphorbia boerhaavioides*, *Euphorbia boliviana*, *Euphorbia bracei*, *Euphorbia brachiata*, *Euphorbia brachycera*, *Euphorbia brandegee*, *Euphorbia brittonii*, *Euphorbia caesia*, *Euphorbia calcicola*, *Euphorbia campestris*, *Euphorbia candelabrum*, *Euphorbia capitellata*, *Euphorbia carmenensis*, *Euphorbia carunculata*, *Euphorbia cayensis*, *Euphorbia celastroides*, *Euphorbia chalicophila*, *Euphorbia chamaerrhodos*, *Euphorbia chamaesula*, *Euphorbia chiapensis*, *Euphorbia chiogenoides*, *Euphorbia cinerascens*, *Euphorbia clarionensis*, *Euphorbia colimae*, *Euphorbia colorata*, *Euphorbia commutata*, *Euphorbia consoquitlae*, *Euphorbia convolvuloides*, *Euphorbia corallifera*, *Euphorbia creberrima*, *Euphorbia crenulata*, *Euphorbia cubensis*, *Euphorbia cuspidata*, *Euphorbia cymbiformis*, *Euphorbia darlingtonii*, *Euphorbia defoliata*,*Euphorbia degeneri*, *Euphorbia deltoidea*, *Euphorbia dentata*, *Euphorbia depressa Euphorbia dictyosperma*, *Euphorbia dictyosperma*, *Euphorbia dioeca*, *Euphorbia discoidalis*, *Euphorbia dorsiventralis*, *Euphorbia drumondii*, *Euphorbia duclouxii*, *Euphorbia dussii*, *Euphorbia eanophylla*, *Euphorbia eggersii*, *Euphorbia eglandulosa*, *Euphorbia elata*, *Euphorbia enalla*, *Euphorbia eriogonoides*, *Euphorbia eriophylla*, *Euphorbia esculaeformis*, *Euphorbia espirituensis*, *Euphorbia esula*, *Euphorbia excisa*, *Euphorbia exclusa*, *Euphorbia exstipitata*, *Euphorbia exstipulata*, *Euphorbia fendleri*, *Euphorbia filicaulis*, *Euphorbia filiformis*, *Euphorbia florida*, *Euphorbia fruticulosa*, *Euphorbia garber*, *Euphorbia gaumerii*, *Euphorbia gerardiana*, *Euphorbia geyeri*, *Euphorbia glyptosperma*, *Euphorbia gorgonis*, *Euphorbia gracilior*, *Euphorbia gracillima*, *Euphorbia gradyi*, *Euphorbia graminea*, *Euphorbia graminiea Euphorbia grisea*, *Euphorbia guadalajarana*, *Euphorbia guanarensis*, *Euphorbia gymnadenia*, *Euphorbia haemantha*, *Euphorbia hedyotoides*, *Euphorbia heldrichii*, *Euphorbia helenae*, *Euphorbia helleri*, *Euphorbia helwigii*, *Euphorbia henricksonii*, *Euphorbia heterophylla*, *Euphorbia hexagona*, *Euphorbia hexagonoides*, *Euphorbia hinkleyorum*, *Euphorbia hintonii*, *Euphorbia hirtula*, *Euphorbia hirta*, *Euphorbia hooveri*, *Euphorbia humistrata*, *Euphorbia hypericifolia*, *Euphorbia* inundata, *Euphorbia involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia latericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinsulicola, Euphorbia longipila, Euphorbia lupulina, Euphorbia lurida, Euphorbia lycioides, Euphorbia macropodoides, macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia microcephala, Euphorbia microclada, Euphorbia micromera, Euphorbia misella, Euphorbia missurica, Euphorbia montana, Euphorbia montereyana, Euphorbia multicaulis, Euphorbia multiformis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidentalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robusta, Euphorbia romosa, Euphorbia rubida, Euphorbia rubrosperma, Euphorbia rupicola, Euphorbia sanmartensis, Euphorbia saxatilis* M. Bieb, *Euphorbia schizoloba, Euphorbia sclerocyathium, Euphorbia scopulorum, Euphorbia senilis, Euphorbia serpyllifolia, Euphorbia serrula, Euphorbia setiloba* Engelm, *Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammilaris, Euphorbia subpeltata, Euphorbia subpubens, Euphorbia subreniforme, Euphorbia subtrifoliata, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaninowii, Euphorbia umbellulata, Euphorbia undulata, Euphorbia vermiformis, Euphorbia versicolor, Euphorbia villifera, Euphorbia violacea, Euphorbia whitei, Euphorbia xanti* Engeim, *Euphorbia xylopoda* Greenm., *Euphorbia yayalesia* Urb., *Euphorbia yungasensis, Euphorbia zeravschanica* and *Euphorbia zinniiflora.*

10. The method according to claim 8 wherein the species of *Euphorbia* is *Euphorbia peplus.*

11. The method according to claim 1 wherein said chemical agent is an angeloyl-substituted ingenane represented by Formula VI or a pharmaceutically acceptable salt thereof.

12. The method according to claim 11 wherein said chemical agent is an ester of an angeloyl substituted ingenane.

13. The method according to claim 12 wherein said ester is an acetylated ester.

14. The method according to claim 1 wherein said chemical agent is 20-O-acetyl-ingenol-3-angelate or an ester thereof or a pharmaceutically acceptable salt of these.

15. The method according to claim 14 wherein said chemical agent is an ester of 20-O-acetyl-ingenol-3-angelate.

16. The method according to claim 1 wherein said chemical agent is an ingenol-3-angelate or an ester thereof or a pharmaceutically acceptable salt of these.

17. The method according to claim 1 wherein said chemical agent is 20-deoxy-ingenol-3-angelate or a pharmaceutically acceptable salt thereof.

18. The method according to claim 17 wherein said chemical agent is an ester of 20-deoxy-ingenol-3-angelate.

19. The method according to claim 16 wherein said chemical agent is an ester of ingenol-3-angelate.

20. The method according to claim 18 wherein said ester is an acetyl ester.

21. The method according to claim 19 wherein said ester is an acetyl ester.

22. The method according to claim 1 wherein said subject is human.

23. The method according to claim 1 wherein $R_{25}$ and $R_{26}$ are OH and $R_{24}$ is hydrogen, O-Acetyl or OH.

24. The method according to claim 1 wherein said chemical agent is ingenol-3-angelate.

* * * * *